US011491263B2

(12) United States Patent
Engel Lopez et al.

(10) Patent No.: US 11,491,263 B2
(45) Date of Patent: Nov. 8, 2022

(54) CONTROLLABLE ION RELEASE CALCIUM PARTICLES, METHOD FOR PRODUCING SAME AND USE THEREOF

(71) Applicants: FUNDACIO INSTITUT DE BIOENGINYERIA DE CATALUNYA (IBEC), Barcelona (ES); UNIVERSITAT POLITECNICA DE CATALUNYA, Barcelona (ES)

(72) Inventors: Elisabeth Engel Lopez, Barcelona (ES); Oscar Castano Linares, Barcelona (ES); Joan Marti Munoz, Barcelona (ES); Josep Anton Planell Estany, Barcelona (ES)

(73) Assignees: FUNDACIO INSTITUT DE BIOENGINYERIA DE CATALUNYA (IBEC), Barcelona (ES); UNIVERSITAT POLITECNICA DE CATALUNYA, Barcelona (ES)

( * ) Notice: Subject to any disclaimer, the term of this patent is extended or adjusted under 35 U.S.C. 154(b) by 215 days.

(21) Appl. No.: 16/618,013

(22) PCT Filed: May 31, 2018

(86) PCT No.: PCT/EP2018/064378
§ 371 (c)(1),
(2) Date: Nov. 27, 2019

(87) PCT Pub. No.: WO2018/220141
PCT Pub. Date: Dec. 6, 2018

(65) Prior Publication Data
US 2020/0108178 A1   Apr. 9, 2020

(30) Foreign Application Priority Data

Jun. 1, 2017  (EP) .................................... 17382325

(51) Int. Cl.
| | |
|---|---|
| *A61L 27/54* | (2006.01) |
| *A61K 8/19* | (2006.01) |
| *A61K 8/33* | (2006.01) |
| *A61K 31/08* | (2006.01) |
| *A61K 33/10* | (2006.01) |
| *A61Q 7/00* | (2006.01) |

(52) U.S. Cl.
CPC ................ *A61L 27/54* (2013.01); *A61K 8/19* (2013.01); *A61K 8/33* (2013.01); *A61K 31/08* (2013.01); *A61K 33/10* (2013.01); *A61Q 7/00* (2013.01); *A61L 2430/30* (2013.01); *A61L 2430/34* (2013.01)

(58) Field of Classification Search
CPC ........ A61L 27/54; A61L 27/10; A61L 27/446; A61L 2430/30; A61L 2430/34; A61K 8/19; A61K 8/33; A61K 33/10; A61K 33/14; A61K 31/08; A61Q 7/00; A61P 19/10

See application file for complete search history.

(56) References Cited

U.S. PATENT DOCUMENTS

| | | | | |
|---|---|---|---|---|
| 4,482,212 | A | * | 11/1984 | Takamatsu ............ G02F 1/1345 349/150 |
| 5,591,453 | A | | 1/1997 | Ducheyne et al. |
| 5,618,549 | A | | 4/1997 | Patat et al. |
| 2007/0258916 | A1 | | 11/2007 | Ferracane et al. |

FOREIGN PATENT DOCUMENTS

| | | | | |
|---|---|---|---|---|
| CN | 102627835 | A | * 8/2012 | |
| EP | 0255629 | A1 | * 2/1988 | ............ C02F 1/5236 |
| EP | 0275688 | A1 | 7/1988 | |
| EP | 2386525 | A1 | 11/2011 | |
| WO | 20030101471 | A1 | 12/2003 | |
| WO | 2011141896 | A1 | 11/2011 | |

OTHER PUBLICATIONS

I. Rajzer, et al, Electrospun gelatin/poly (β-caprolactone) fibrous scaffold modified with calcium phosphate for bone tissue engineering; Materials Science Engineering; C44; 2014; pp. 183-190.
Y. Sun, et al; A low-temperature sol-gel route for the synthesis of bioactive calcium silicates; Chinese Chemical Letters; 24 (2); 2013; pp. 170-172.
C. Wang, et al; Bioactive nanoparticle through postmodification of colloidal silica; Applied Materials and Interfaces; 6 (7); 2014; pp. 4935-4939.
R.A. Martin, et al; Characterizing the hierarchical structures of bioactive sol-gel silicate glass and hybrid scaffolds for bone regeneration; Philosophical Transactions of The Royal Society A; 370; 2012; pp. 1422-1443.
S.L. Greasley, et al; Controlling particle size in the Stober process and incorporation of calcium; Journal of Colloid and Interface Science; 469; 2016; pp. 213-223.
V. Uskokovic, et al; Phase composition control of calcium phosphate nanoparticles fortunable drug delivery kinetics and treatment of osteomyelitis; Journal of Biomedical Materials Research, Part A; 101A; 2013; pp. 1416-1426.

(Continued)

*Primary Examiner* — Ali Soroush
(74) *Attorney, Agent, or Firm* — Lucas & Mercanti, LLP

(57) ABSTRACT

The present invention refers to a method for the synthesis of a biodegradable calcium release material that shows controlled ion release properties for tissue engineering, biomaterials containing the calcium particles as well as the calcium particles obtainable therefrom. By varying the treatment temperature of the described method, the calcium material shows different calcium release profiles. Contrary to a specific chemical composition such as $CaCO_3$ which is associated to a specific calcium release profile, the present invention allows a manifold of compositions, with a manifold of calcium release profiles, all starting from a single specific chemical composition calcium precursor. Therefore, the invention also relates to the use of the controllable release, calcium material in tissue regeneration such as wound healing processes.

17 Claims, 15 Drawing Sheets

(56) References Cited

OTHER PUBLICATIONS

S. Dasgupta, et al; Reverse micelle mediated synthesis of calcium phosphate nanocarriers for controlled release of bovine serum albumin; Acta Biomaterials; 5 (8); 2009; pp. 3112-3121 (24 pages).
B. Yu, et al; Effect of calcium source on structure and properties of sol-gel derived bioactive glasses; Langmuir; 28 (50); 2012; pp. 17465-17476.
S. Bettini, et al; Food-grade TiO2 impairs intestinal and systemic immune homeostasis, initiates preneoplastic lesions and promotes aberrant crypt development in the rat colon; Scientific Reports; vol. 7; 2017; pp. 40373 (13 pages).
W. Wood, et al; Wound healing: calcium flashes illuminate early events; Current Biology; 22 (1); 2012; pp. R14-R16.
W. Wood, et al; Calcium flashes orchestrate the wound inflammatory response through DUOX activation and hydrogen peroxide release; Current Biology; 23 (5); 2013; pp. 424-429.
M. Navarro, et al; Cellular response to calcium phosphate glasses with controlled solubility; Journal of Biomedical Materials Research; 67 (3); 2003; pp. 1009-1015.
A. Mikolajczyk, et al; Zeta potential (#) for metal oxide nanoparticles: A predictive model developed by nano-QSPR approach; Chemical of Materials; 27 (7); 2015; pp. 2400-2407 (12 pages).
N. Sachot, et al; Hybrid organic-inorganic scaffolding biomaterials for regenerative therapies; Current Organic Chemistry; 18 (18); 2014; pp. 2299-2314 (22 pages).
P. Wang, et al; Bone tissue engineering via nonostructured calcium phosphate biomaterials and stem cells; Bone Research; 2, 2014; Article No. 14017; 13 pages.
L. Moulin; Synthesis of new precursors for the fabrication of fully organic hybrid nanofibers; (Bachelor's Degree Final Project, supervisor: Castaño Linares, Óscar), 2014; 82 pages.
C. Qin, et al; CO2 capture performance and attrition property of CaO-based pellets manufactured from organometallic calcium precursors by extrusion; Energy and Fuels; 28; 2014; pp. 329-339.
X. Wang, et al; Amorphous polyphosphate/amorphous calcium carbonate implant material with enhanced bone healing efficacy in a critcal-size defect in rats; Biomedical Materials; 11 (3); 2016; pp. 035005 (13 pages).
F. Foroutan, et al; Sol-gel synthesis and electrospraying of biodegradable (P2O5)55—(CaO)30—(Na2O)15 glass nanospheres as a transient contrast agent for ultrasound stem cell imaging; ACS Nano; 9 (2); 2015; pp. 1868-1877 (29 pages).
A. Valor, et al; Thermal decomposition of the calcium salts of several carboxylic acids; Thermochimica Acta; 389; 2002; pp. 133-139.
International Search Report dated Jul. 17, 2018 for PCT/EP2018/064378.

* cited by examiner

A

B

CONTROLLABLE ION RELEASE CALCIUM PARTICLES, METHOD FOR PRODUCING SAME AND USE THEREOF

CROSS REFERENCE TO RELATED APPLICATION

This Application is a 371 of PCT/EP2018/064378 filed on May 31, 2018 which, in turn, claimed the priority of European Patent Application No. 17382325.3 filed on Jun. 1, 2017, both applications are incorporated herein by reference.

FIELD OF THE INVENTION

The present invention relates to calcium particles that show controlled ion release properties and a method for producing said particles, for tissue engineering biomaterials containing said calcium particles as well as to the calcium particles obtainable therefrom.

BACKGROUND

Hard and soft tissue damage generally triggers a robust and successful wound healing response, which is associated with an increase in calcium concentration around the damaged tissue (see for example, Wood W. et al., Wound healing calcium flashes illuminate early events, Current Biology, 2001, 22(1), R14-R16 and Wood, W et al., Calcium flashes orchestrate the wound inflammatory response through DUOX activation and hydrogen peroxide release, Current Biology, 2003, 23(5), 424-429).

Biocompatible scaffolds comprising calcium have been known since the 70's. In particular, phosphate-based glasses ($P_2O_5$—CaO—$Na_2O$—$TiO_2$) have unique dissolution properties in aqueous-based fluids. Degradation rates (and solubility) can be varied from hours to several weeks by tuning their chemical composition. Furthermore, these glasses can be synthesized to include modifying oxides that are able to induce a specific biological function, enhance biocompatibility and induce controlled release of certain ions (see, for instance, EP 2 386 525 A1). Calcium ions are known to stimulate cell homing and cell proliferation, and calcium phosphate-based glasses have been shown to be biocompatible (see Navarro M. et al., Cellular response to calcium phosphate glasses with controlled solubility, Journal of Biomedical Materials Research, 2003, 67(3), 1009-1015). Therefore, calcium phosphate-based glasses find potential clinical uses as bone cavity fillers, drug delivery systems, biodegradable reinforcing phases in the case of composites for bone fixation devices, tissue engineering scaffolds but also in tissue regeneration engineering process.

Most phosphate-based glasses are prepared by melt-quenching methods. A mixture of oxide precursors is melted in a furnace at temperatures of over 1000° C.; the final composition of the glass depends on the ratio of the precursors. Once a homogeneous melt has been achieved, the glass is formed by casting different shapes as plates. To remove residual stress, the melts are normally annealed at the glass transition temperature (Tg) and cooled very slowly to room temperature.

The sol-gel process offers low-temperature processing along with the homogeneous mixing of the reactants, leading to better quality glasses with a more easily controlled morphology. A typical process starts with a solution of the comprised elements involved in the final product, which reacts with water to produce colloidal particles. This suspension is commonly known as "sol". Typical precursors are inorganic alkoxides, which undergo hydrolysis and polycondensation reactions to form a colloid, and metal chlorides.

WO 2011/141896, and its priority application EP2386525, describe sol-gel nanostructured materials for bone tissue regeneration comprising a glass with the following molar composition on an oxide basis: from 5 to 60% CaO, from 30 to 60% $P_2O_5$, up to 60% MgO, 0%<$TiO_2$<25%, up to 25% $Na_2O$ and/or up to 25% $K_2O$.

EP0275688 describes a manufacturing process to obtain metal oxides from organometallic compounds by means of alkaline hydrolysis reactions in an organic medium. The organic ligands are generally a hydrocarbon group bonded via an oxygen atom, such as a lower alkyl or alkylene.

In Uskokovic V. and Desai T. A., J. Biomed. Mater. Res. Part A, 2013, 101A, 1416-1426 and in Dasgupta, S. et al., Acta Biomater., 2009, 5(8), 3112-3121 the authors describe calcium phosphate (CAP) nanoparticles for tuneable drug delivery.

Yu, Bobo, et al., Langmuir, 2012, 28(50), 17465-17476 describe the use of different calcium precursors (nitrate, chloride or 2-methoxyethoxide) for low temperature (<130° C.) sol-gel synthesis (Si, P and Ca) and assess their potential for the production of bioactive hybrids for bone regeneration composed of Si, Ca and also P.

WO 2003/101471 discloses a calcium-containing composition obtained from animal bone tissue for treating disorders connected with the growth or healing of bones or bone tissue, wherein the composition is a calcium phosphate complex having a protein content of less than 25 wt. %.

U.S. Pat. No. 5,618,549 discloses biocompatible and bio-absorbable calcium salts in the form of particles for the treatment of certain bone diseases.

However, all mentioned above materials involve complex mixtures of precursor materials and show far from ideal effective implantable biomaterial properties since they do not disperse in a stable manner within typical biomaterial polymer matrices, such as polylactic acid. Moreover, in some cases the ion release rate of said materials is extremely slow, in the range of hundreds of days (up to 500 days) and in all of them the release rate depends on the initial concentration of the components (e.g. titanium ratio) so, for obtaining different release ratios, a completely new synthetic procedure is required with different precursor concentrations. Additionally, the phosphate-based glass materials not only release calcium ions but also sodium, phosphates and titanium ions which may have undesirable side effects such as producing hypernatremia or other toxicity problems. Recent evidence shows that intake of $TiO_2$ impairs intestinal and systemic immune homeostasis, initiates preneoplastic lesions and promotes aberrant crypt development in the rat colon (Bettini, S. et al., Scientific Reports, 2017, vol. 7, p. 40373).

Therefore, no solution has yet been proposed for a biodegradable calcium release material free from Ti, P or Na components, which shows a controllable release rate in a biologically relevant amount of time, and which does not require complicated synthetic procedures.

SUMMARY OF THE INVENTION

The present invention now offers a solution to these problems, relating to a method of preparing a calcium material characterised by showing tuneable calcium release properties, wherein the release rate of said calcium material can be adjusted by selecting the treatment temperature of calcium alkoxyalkoxide particles used in the preparation of the calcium material. The present invention also relates to materials comprising exclusively $Ca(OH)_2$, $CaCO_3$, CaO and an organic fraction (<1.5%).

Generally, submitting a calcium alkoxyalkoxide in solid form to a moderate temperature treatment (between 70 and 200° C.) yields calcium particles that show high initial calcium release rates (high release bursts) with very low release rates after the initial first hour (see FIG. 4). Surprisingly, the inventors have found that when submitting said calcium alkoxyalkoxide materials to temperatures ranging from 300 to 600° C., they show a slow steady $Ca^{2+}$ release rate (at least 5 days) together with a reduced initial calcium release rate (initial burst). Therefore, the higher the temperature, the lower the initial burst and the longer the sustained release of calcium ions. Contrary to a specific chemical composition such as $CaCO_3$ which is characterised by a specific calcium release profile, the present invention discloses a simple process to obtain a manifold of chemical compositions simply arising from tuning the temperature treatment of the alkoxyalkoxide calcium material, allowing the tuning of the calcium release profiles. Therefore, the present invention relates to the field of controlled ion release for tissue engineering purposes.

Accordingly, in a first aspect, the invention is directed to a calcium material, of general formula (I):

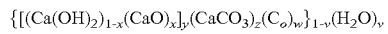

wherein $0 \leq x \leq 1$, $0.06 \leq y \leq 0.75$, $0.14 \leq z \leq 0.93$, $0.01 \leq w \leq 0.11$, $0 \leq v \leq 0.44$ and $C_o$ designates a carbon containing fraction comprising one or more compounds selected from the group consisting of calcium alkoxyalkoxide, alkoxyalcohol, alcohol, calcium alkoxide, graphite and combinations thereof.

In a second aspect, the invention is directed to a method for the preparation of a calcium material of general formula (I), comprising the steps of:
a) Preparing at least one calcium alkoxyalkoxide of general formula $Ca(OAOR_1)_2$ in solid form, wherein A is a divalent $C_1$-$C_6$, optionally substituted, linear or branched alkyl chain and $R_1$ is a $C_1$-$C_6$ linear or branched alkyl chain or $C_6$-$C_{12}$ aryl; and
b) Submitting the at least one calcium alkoxyalkoxide in solid form of step (a) to a temperature treatment of between 70° C. and 600° C.

In a third aspect, the invention relates to the calcium material obtainable by the method of the invention. The inventors have observed that by varying the treatment temperature, the calcium material as defined above shows different calcium release profiles.

Therefore, in a fourth aspect, the invention is directed to a biocompatible matrix comprising the calcium material of aspects one or three.

In a fifth aspect, the invention relates to the calcium material of aspects one or three or to the biocompatible matrix of aspect four for use in tissue regeneration, preferably selected from the group consisting of wound healing, bone regeneration, skin regeneration, muscle regeneration, cardiac regeneration and promotion of vascularization.

In a sixth aspect, the invention is directed to the use of the calcium material of aspects one or three or the biocompatible matrix of aspect four for the cosmetic regeneration of hair.

DESCRIPTION OF THE DRAWINGS

These and other characteristics and advantages of the invention will become clearly understood in view of the detailed description of the invention which becomes apparent from preferred embodiments of the invention, given just as an example and not being limited thereto, with reference to the drawings.

DETAILED DESCRIPTION OF THE INVENTION

Figure 1:
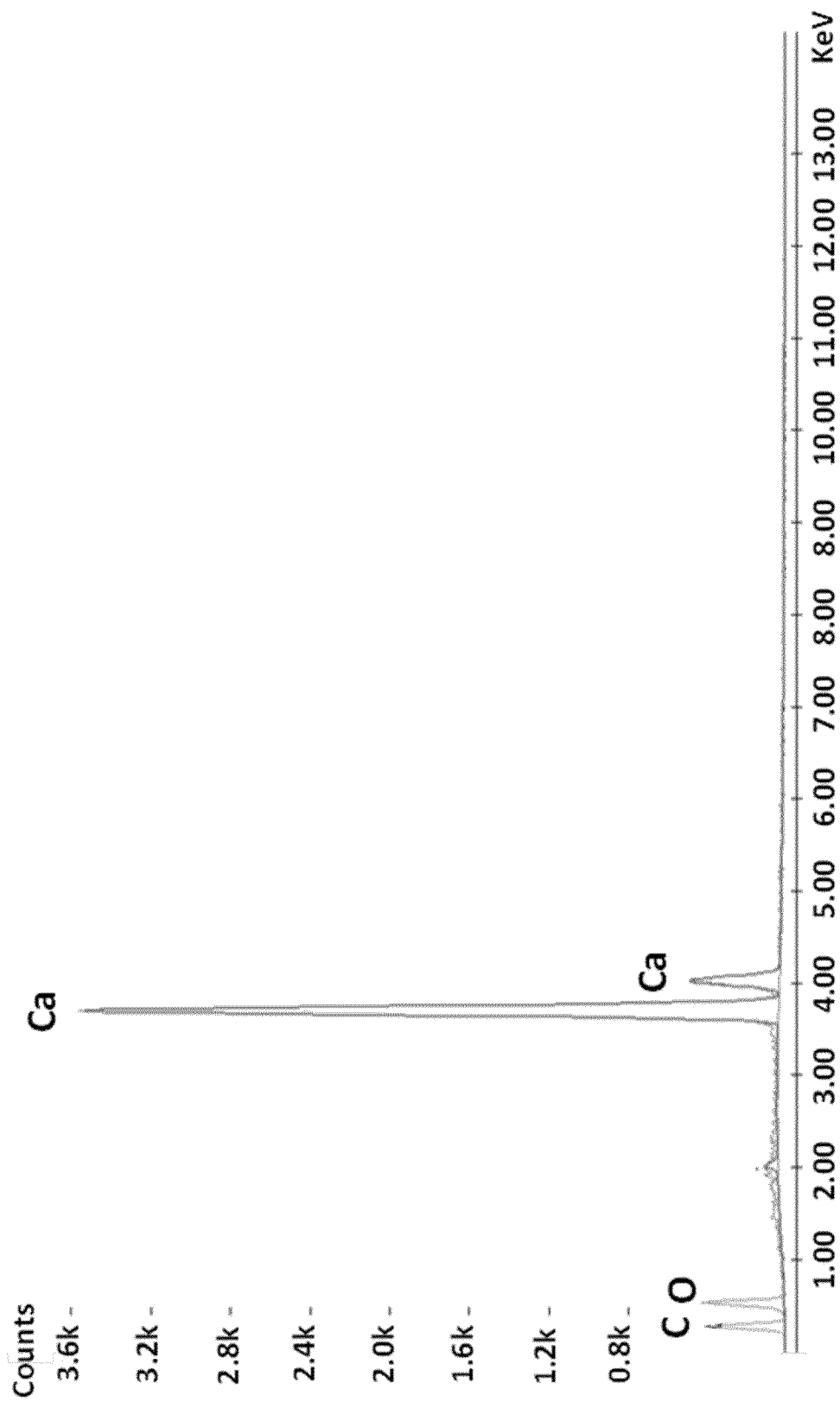
FIG. 1: Energy Dispersive Spectroscopy (EDS) spectrum of sample Ca400 showing the presence of Ca, O and C elements.

Unless defined otherwise, all technical and scientific terms and expressions used herein have the same meaning as commonly understood to one of ordinary skill in the art to which this disclosure belongs. Each aspect or embodiment as defined herein may be combined with any other aspect(s) or embodiment(s) unless clearly indicated to the contrary. In particular, any features indicated as being preferred may be combined with any other feature indicated as being preferred.

The first aspect of the invention is directed to a calcium material, of general formula (I):

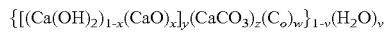
$\{[(Ca(OH)_2)_{1-x}(CaO)_x]_y(CaCO_3)_z(C_o)_w\}_{1-v}(H_2O)_v$ wherein $0 \leq x \leq 1$, $0.06 \leq y \leq 0.75$, $0.14 \leq z \leq 0.93$, $0.01 \leq w \leq 0.11$, $0 \leq v \leq 0.44$ and $C_o$ designates a carbon containing fraction comprising one or more compounds selected from the group consisting of calcium alkoxyalkoxide, alkoxyalcohol, alcohol, calcium alkoxide, graphite and combinations thereof.

In a particular embodiment, the carbon fraction may further comprise saturated or unsaturated hydrocarbon molecules selected from alkanes, alkenes, alkynes, cycloalkanes and/or aromatic hydrocarbons.

The carbon-containing fraction is to be understood as the relative amount of compounds resulting from submitting a calcium alkoxyalkoxide as defined below to the method of the invention. Therefore, in an embodiment, the calcium material of the invention is a material wherein the carbon-containing fraction is the result of submitting a calcium alkoxyalkoxide of general formula $Ca(OAOR_1)$, wherein A is a divalent $C_1$-$C_6$ linear or branched alkyl chain and $R_1$ is a $C_1$-$C_6$ linear or branched alkyl chain, to a process of thermolysis.

In another embodiment, said A and $R_1$ are linear alkyl chains. In another preferred embodiment, at least one of A or $R_1$ is a linear alkyl chain. In yet another particular embodiment, A is an optionally substituted linear alkyl chain.

In an embodiment, at least one of A or $R_1$ is a branched alkyl chain. Preferably, said A and $R_1$ are branched alkyl chains. In yet another preferred embodiment, at least one of A or $R_1$ is an unsubstituted linear or branched alkyl chain. In a particular embodiment, said A and $R_1$ are unsubstituted linear or branched alkyl chains.

In a preferred embodiment, the calcium material of the invention is a material wherein the carbon-containing fraction is the result of submitting a calcium alkoxyalkoxide of general formula $Ca(OAOR_1)$, wherein A is a divalent $C_1$-$C_6$, optionally substituted, linear or branched alkyl chain and $R_1$ is a $C_1$-$C_6$ linear or branched alkyl chain or $C_6$-$C_{12}$ aryl, to a process of thermolysis.

In a further preferred embodiment of the invention, in the calcium material of the invention, the carbon-containing fraction is the result of submitting a calcium alkoxyalkoxide of general formula $Ca(OAOR_1)$, selected from those in which $R_1$ is methyl, ethyl, propyl or phenyl, and A is $(CH_2)_n$ with n=1, 2 or 3 optionally substituted and optionally branched as defined below, to a process of thermolysis.

In a further preferred embodiment of the invention, in the calcium material of the invention, the carbon-containing fraction is the result of submitting a calcium alkoxyalkoxide of general formula $Ca(OAOR_1)$, selected from those in which $R_1$ is methyl, ethyl or propyl and A is $(CH_2)_n$ with n=1, 2 or 3, more preferably, wherein $R_1$ is methyl and A is $(CH_2)_2$ to a process of thermolysis.

In a preferred embodiment of the invention, the carbon-containing fraction is a carbon-containing fraction wherein the alkoxyalkoxide in the calcium alkoxyalkoxide is an alkoxyalkoxide of general formula $R_1OAO^-$, wherein A is a divalent $C_1$-$C_6$ linear or branched alkyl chain and $R_1$ is a $C_1$-$C_6$ linear or branched alkyl chain; is a carbon-containing fraction wherein the alkoxyalcohol is an alkoxyalcohol of general formula $R_1OAOH$, wherein A is a divalent $C_1$-$C_6$ linear or branched alkyl chain and $R_1$ is a $C_1$-$C_6$ linear or branched alkyl chain; is a carbon-containing fraction wherein the alcohol is linear or branched $C_1$-$C_6$ alkyl alcohol and/or is a carbon-containing fraction wherein the calcium alkoxide is linear or branched $C_1$-$C_6$ alkyl calcium alkoxide.

In a further preferred embodiment of the invention, the carbon-containing fraction is a carbon-containing fraction wherein the alkoxyalkoxide in the calcium alkoxyalkoxide is an alkoxyalkoxide of general formula $R_1OAO^-$, wherein A is a divalent $C_1$-$C_6$, optionally substituted, linear or branched alkyl chain and $R_1$ is a $C_1$-$C_6$ linear or branched alkyl chain or $C_6$-$C_{12}$ aryl; is a carbon-containing fraction wherein the alkoxyalcohol is an alkoxyalcohol of general formula $R_1OAOH$, wherein A is a divalent $C_1$-$C_6$ linear or branched alkyl chain and $R_1$ is a $C_1$-$C_6$ linear or branched alkyl chain or $C_6$-$C_{12}$ aryl; is a carbon-containing fraction wherein the alcohol is linear or branched, optionally substituted, $C_1$-$C_6$ alkyl alcohol or $C_6$-$C_{12}$ aryl alcohol and/or is a carbon-containing fraction wherein the calcium alkoxide is linear or branched, optionally substituted, $C_1$-$C_6$ alkyl calcium alkoxide or $C_6$-$C_{12}$ aryl calcium alkoxide.

In another preferred embodiment of the invention, the carbon-containing fraction is selected from the group comprising calcium 2-methoxyethoxide, calcium 2-methoxypropoxide, calcium 3-methoxypropoxide, calcium 3-methoxybutoxide, calcium 4-methoxybutoxide, calcium 2-ethoxyethoxide, calcium 2-propoxyethoxide, calcium 3-propoxypropoxide, calcium ethoxide, calcium methoxide, 2-methoxyethanol, 2-methoxypropanol, 3-methoxypropanol, 3-methoxybutanol, 4-methoxybutanol, 2-ethoxyethanol, 2-propoxyethanol, 3-propoxypropanol, methanol, ethanol, propanol, butanol, graphite, or combinations thereof.

In the context of the present invention, and as described below, the calcium precursors are readily recognizable by the skilled person as calcium complexes comprising two ligands.

In yet another preferred embodiment of the invention, the carbon-containing fraction is selected from the group comprising calcium 2-methoxyethoxide, calcium 1,3-diethoxy-2-propoxide, calcium 2-methoxypropoxide, calcium 3-methoxypropoxide, calcium 3-methoxybutoxide, calcium 4-methoxybutoxide, calcium 2-ethoxyethoxide, calcium 1-ethoxy-2-propoxide, calcium 2-propoxyethoxide, calcium 3-propoxypropoxide, calcium 1-methoxy-2-propoxide, calcium 1-methoxy-2-butoxide, calcium 2-phenoxyetoxide, calcium ethoxide, calcium methoxide, 2-methoxyethanol, 1,3-diethoxy-2-propanol, 2-methoxypropanol, 3-methoxypropanol, 3-methoxybutanol, 4-methoxybutanol, 2-ethoxyethanol, 1-ethoxy-2-propanol, 2-propoxyethanol, 3-propoxypropanol, 1-methoxy-2-propanol, 1-methoxy-2-butanol, 2-phenoxyetanol, methanol, ethanol, propanol, butanol, graphite, or combinations thereof.

In the context of the present invention, the terms alkoxide, methoxide and ethoxide refer to the conjugate base of an alcohol bearing calcium as counter-ion. Therefore, the term alkoxide is to be understood as calcium alkoxide.

In both the context of the present invention and as widely recognized in the art, "branched alkyl chain" refers to an alkyl chain which comprises at least one secondary $C_1$-$C_6$ alkyl chain attached to any one of the carbon atoms forming the primary alkyl chain. In this way, non-limiting examples of a secondary $C_1$-$C_6$ alkyl chain are —$CH_3$, —$CH_2CH_3$ or —$CH_2CH_2CH_3$. Naturally, a branched primary alkyl chain will have at least one of the H in a $CH_2$ moiety replaced by said secondary alkyl chain.

The term "substituted" or its antonym "unsubstituted" refers to the presence, or absence, respectively, of substituent groups commonly known in the art. In a preferred embodiment, the substituent is selected from the group consisting of —$(CH_2)_n$OR', —$(CH_2)_n$NR'R', —$(CH_2)_n$CONR'R', —$(CH_2)_n$NR'COR', —F, —Cl, —Br, and —I, wherein n is an integer selected from 0 to 6 and R' is independently selected from H, $C_1$-$C_6$ linear or branched alkyl chain and $C_6$-$C_{12}$ optionally substituted aryl. In a more preferred embodiment, the substituent described above is selected from the group consisting of —$(CH_2)_n$OR' and —$(CH_2)_n$NR'R', more preferably from —$(CH_2)_n$OR'. In another preferred embodiment, the integer n described above is an integer selected from 0 to 3 and R' described above is independently selected from H, $C_1$-$C_3$ linear alkyl chain and phenyl. A non-limiting example of a substituent group would be —OH or —$CH_2$—O—$CH_2CH_3$.

The term "aryl" refers to a $C_6$-$C_{12}$ aryl group. A "$C_6$-$C_{12}$ aryl" refers to a radical substituent comprising 1 to 2 fused aromatic rings comprising from 6 to 12 carbon atoms, preferably 6 carbon atoms. In a particular embodiment, aryl is phenyl.

In the context of the present invention, the calcium material is a solid mixture of compounds in which the majority of said compounds comprise calcium cations.

In a preferred embodiment of the invention, the calcium material of the invention is a material having a calcium content comprised between 35%-55% by weight, preferably from 40% to 51% by weight. The remainder elements that add up to the total weight of said calcium material are C, O and H. It is thus evident that the material of the invention is substantially devoid of P or Ti atoms. In a preferred embodiment, the material of the invention does not comprise P nor Ti atoms.

In yet another particular embodiment of the invention, the calcium material as defined above is a calcium material in the form of particles, preferably microparticles and nanoparticles. In a preferred embodiment, the calcium material as defined above is in the form of nanoparticles. The term "nanoparticle" used herein may encompass a particle having all dimensions of from 1 to 100 nm. The term "microparticle" used herein may encompass a particle having all dimensions superior to at least 100 nm. For example, when the particles are in the form of a sphere, the dimension will be the diameter of the sphere. Particle sizes may be determined by techniques such as, electron microscopy (TEM/FE-SEM) or Dynamic Light Scattering (DLS) techniques.

The second aspect of the invention provides a method for the preparation of a calcium material, comprising the steps of:
a) Preparing at least one calcium alkoxyalkoxide material of general formula Ca(OAOR$_1$)$_2$ in solid form, wherein A is a divalent $C_1$-$C_6$ linear or branched alkyl chain and $R_1$ is a $C_1$-$C_6$ linear or branched alkyl chain or $C_6$-$C_{12}$ aryl; and
b) Submitting the at least one calcium alkoxyalkoxide in solid form of step (a) to a temperature treatment of between 70° C. and 600° C.

In a particular embodiment of the second aspect, A in step (a) is a divalent $C_1$-$C_6$, optionally substituted, linear or branched alkyl chain and $R_1$ is a $C_1$-$C_6$ linear or branched alkyl chain or $C_6$-$C_{12}$ aryl.

The precise composition of the calcium material formula (I) of the present invention (i.e., the values of x, y, z, w and v) can be adjusted within definable ranges by simply selecting the temperature of step (b). By adjusting said temperature, the inventors have surprisingly found that a range of several calcium materials with different release profiles is obtained.

In the context of the present invention, a $C_1$-$C_6$ alkyl chain is a chain of 1, 2, 3, 4, 5 or 6 carbon atoms derived from an alkane which misses one hydrogen atom. On a particular embodiment, the alkyl chain of the calcium alkoxyalkoxide is a linear alkyl chain. On yet another particular embodiment, said alkyl chain is a branched alkyl chain. The divalent $C_1$-$C_6$ linear or branched alkyl chain A is to be understood as an alkyl chain as defined above but which misses one hydrogen atom from each extremity of the chain, as so it forms a bridging chain between two oxygen atoms of the calcium alkoxyalkoxide. In a particular embodiment, the divalent alkyl chain A is a divalent linear alkyl chain. In yet another particular embodiment, the divalent alkyl chain is a divalent branched alkyl chain. In a particular embodiment, the alkyl chains as described above, A and $R_1$, are unsubstituted linear chains.

Non-limiting examples of calcium alkoxyalkoxides of general formula Ca(OAOR$_1$)$_2$ as mentioned above are calcium 2-methoxyethoxide, calcium 1,3-diethoxy-2-propoxide, calcium 2-methoxypropoxide, calcium 3-methoxypropoxide, calcium 3-methoxybutoxide, calcium 4-methoxybutoxide, calcium 2-ethoxyethoxide, calcium 1-ethoxy-2-propoxide, calcium 2-propoxyethoxide, calcium 3-propoxypropoxide, calcium 1-methoxy-2-propoxide, calcium 1-methoxy-2-butoxide and calcium 2-phenoxyetoxide. In a particular embodiment, $R_1$ is selected from methyl, ethyl and phenyl. In another particular embodiment, A is selected from a linear or branched, optionally substituted $C_1$-$C_3$ alkyl chain. Preferably, the calcium alkoxyalkoxide is selected from calcium 2-methoxyethoxide, calcium 1,3-diethoxy-2-propoxide, calcium 2-ethoxyethoxide, calcium 1-ethoxy-2-propoxide, calcium 1-methoxy-2-propoxide, calcium 1-methoxy-2-butoxide and calcium 2-phenoxyetoxide. On a particular embodiment, $R_1$ is methyl and A is $(CH_2)_2$, i.e., in a preferred embodiment, the at least one calcium alkoxyalkoxide is calcium 2-methoxyethoxide.

In a particular embodiment, the calcium alkoxyalkoxide in solid form of step (a) is isolated prior to submitting it to the temperature treatment of step (b). It is apparent to the skilled person in the context of the present invention, that isolating a solid product involves generally one or several of the following steps: filtration or vacuum filtration, centrifugation, evaporation, sublimation. In a particular embodiment, the isolation step is performed by centrifugation. In another particular embodiment, the isolation step is performed by filtration or vacuum filtration. In another particular embodiment, the isolated calcium alkoxyalkoxide in solid form is dried at a temperature of between 25° C. and 75° C. for a period of 30 minutes to 8 hours. Optionally, the dried solid calcium alkoxyalkoxide is ground before submitting it to step (b).

The inventors have observed that by varying the treatment temperature, the obtainable calcium material by the process defined above surprisingly shows different calcium release profiles.

Without being bound to theory, it is believed that it is the thermal energy applied on the calcium alkoxyalkoxide what allows tuning the chemical composition of the resulting calcium material, producing calcium particles that comply with a specific $Ca^{2+}$ release profile. Once submitted to the temperature treatment, the calcium particles are no longer composed strictly of a single calcium alkoxyalkoxide and their exact composition is a mixture of calcium compounds at different ratios, ratios that depend on the conditions of the applied thermal treatment.

Increasing the temperature decomposes organic molecules leading to the formation of calcium hydroxide, Ca(OH)$_2$, and organic compounds as defined above. Further increasing the temperature results in the formation of calcium carbonate, CaCO$_3$ at the cost of Ca(OH)$_2$, and organic compounds. Finally, upon heating at 500° C., the resulting calcium material is believed to be predominantly calcium carbonate and CaO (<10%). The method of the present invention allows obtaining a manifold of compositions, with a manifold of calcium release profiles, all starting from a single specific chemical composition of at least one calcium alkoxyalkoxide. Therefore, depending on the applied temperature, the following reaction is believed to provide the products with a molar ratio from 0 to 1:

Ca(OAOR$_1$)$_2$→Ca(OAOR$_1$)$_2$+Ca(OH)$_2$+CaCO$_3$+ CaO+organic compounds wherein A, R$_1$ and the organic compounds are as defined above. In order to characterise the composition of the calcium materials obtainable by the method of the present invention, the inventors have measured the total amount of carbon atoms (Total Carbon Content, TCC) which comprises carbon atoms of both CaCO$_3$ and organic compounds of exemplary calcium material samples. Additionally, the total amount of carbon atoms found in organic molecules (Total Organic Carbon) of the same exemplary calcium material samples has also been measured. Accordingly, the composition of the calcium material obtainable by the process of the invention as defined above, has the following formula:

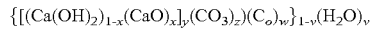
$\{[(Ca(OH)_2)_{1-x}(CaO)_x]_y(CO_3)_z)(C_o)_w\}_{1-v}(H_2O)_v$ wherein 0≤x≤1, 0.06≤y≤0.75, 0.14≤z≤0.93, 0.01≤w≤0.11, 0≤v≤0.44 and C$_o$ designates a carbon containing fraction comprising one or more compounds selected from the group consisting of calcium alkoxyalkoxide, alkoxyalcohol, alcohol, graphite and combinations thereof.

The term "Z-potential" as used herein may encompass the potential difference between a dispersion medium and the stationary layer of fluid attached to a dispersed particle. Z-potential may be measured by electrophoresis based techniques.

Particles produced by this method have a positive charged surface (Z-potential) in contrast with mainly metal particle oxides (Chem. Mater., 2015, 27 (7), pp 2400-2407). This aspect enhances polymer-particle interactions in thermoplastic aliphatic polyesters like polylactic acid or polycaprolactone, which are characterized to be negatively charged. Wettability is improved and also their mechanical properties (shear stress) due to the minimization of the pores and maximization of the contacted surface in the interface between the particle and the polymeric matrix.

Additionally, particles produced by this method are not fully inorganic and are generally soft compared to oxides and carbonates. That reduces the stiffness of the composites where these particles are involved making them more compatible for soft tissue regeneration (Curr. Org. Chem. 18, 18, 2299-2314, 2014) in contrast to full inorganic nanoparticles, which increase the stiffness of composites targeting bone regeneration (Bone Research 2, Article number: 14017 2014).

In a particular embodiment of the invention, the method for the preparation of a calcium material as defined above is a method wherein in step (b) the at least one calcium alkoxyalkoxide in solid form of step (a) is submitted to a temperature treatment of between 70° C. to 600° C., more preferably 100 to 600° C., even more preferably from 100 to 500° C. In general, the inventors have observed two temperature regimes: one between 70° C. and 200° C. in which the controllable release calcium material as defined above shows a calcium release rate characterised by an initial burst of calcium release with very low release rates after the initial first hour; and a second one between 200° C. and 600° C. in which the controllable release calcium material as defined above shows a calcium release rate characterised by a much lower initial burst of calcium release followed by a sustained, practically linear controlled release of calcium throughout the experiment (up to several days).

Surprisingly, the inventors have found out that the present calcium material shows a completely unexpected controllable calcium-release behaviour since the materials previously known in the art require complex mixtures to achieve the same result, usually comprising atoms of titanium and/or phosphorous. Examples of such complex mixtures are phosphate glasses of formula P$_2$O$_5$—CaO—Na$_2$O—TiO$_2$. In addition, other related formulations do not show the same behaviour, as detailed below in comparative example 9.

In another preferred embodiment of the present invention, the method for the preparation of a controllable release, calcium material is a method wherein the calcium alkoxyalkoxide material is submitted to a temperature treatment for a time period of 1 to 24 hours, preferably from 6 to 14 hours.

In a preferred embodiment of the invention, the step of preparing at least one calcium alkoxyalkoxide in solid form as defined above comprises:
a1. dissolving metal calcium at reflux temperature in an alkoxyalcohol of general formula R$_1$OAOH, wherein A is a divalent C$_1$-C$_6$ linear or branched alkyl chain and R$_1$ is a C$_1$-C$_6$ linear or branched alkyl chain;
a2. optionally, cooling down to room temperature;
a3. diluting with an organic solvent;
a4. adding an aqueous base; and
a5. ageing the solution obtained in step (a4) at room temperature.

In a particular embodiment in step a1 of the preferred embodiment above, A is a divalent C$_1$-C$_6$, optionally substituted, linear or branched alkyl chain and R$_1$ is a C$_1$-C$_6$ linear or branched alkyl chain or C$_6$-C$_{12}$ aryl.

Step (a1) is optionally conducted under inert atmosphere, preferably under Argon atmosphere. In a particular embodiment, step (a1) involves maintaining the reflux temperature for a time frame comprised between 6 hours to 4 weeks, preferably from 12 hours to 3 weeks, depending on the time required to achieve complete consumption of the reactants.

Suitable alkoxyalcohol solvents of general formula R$_1$OAOH are for example, but not limited to, those in which R$_1$ is methyl, ethyl, propyl, butyl, pentyl, hexyl and phenyl and A is (CH$_2$)$_n$ with n=1 to 6 or C$_1$-C$_3$ optionally substituted, branched alkyl chain as defined above. Non-limiting examples of alkoxyalcohols contemplated herein are 2-methoxyethanol, 1,3-diethoxy-2-propanol, 2-methoxypropanol, 3-methoxypropanol, 3-methoxybutanol, 4-methoxybutanol, 2-ethoxyethanol, 1-ethoxy-2-propanol, 2-propoxyethanol, 3-propoxypropanol, 1-methoxy-2-propanol, 1-methoxy-2-butanol and 2-phenoxyetanol.

In a preferred embodiment, R$_1$ is methyl, ethyl or propyl and A is (CH$_2$)$_n$ with n=1, 2 or 3, more preferably, R$_1$ is methyl and A is (CH$_2$)$_2$. In a more preferred embodiment, R$_1$ is methyl, ethyl or phenyl and A is (CH$_2$)$_n$ with n=1, 2 or 3 or C$_1$-C$_3$ branched alkyl chain as defined above, most preferably, R$_1$ is methyl or ethyl and A is (CH$_2$)$_2$, —CH(CH$_3$)CH$_2$—, —CH(CH$_2$CH$_3$)CH$_2$— or —CH(CH$_2$OCH$_2$CH$_3$)CH$_2$—. In an even more preferred embodiment, the alkoxyalcohol solvent is 2-methoxyethanol, 1,3-diethoxy-2-propanol, 2-ethoxyethanol, 1-ethoxy-2-propanol, 1-methoxy-2-propanol, 1-methoxy-2-butanol and 2-phenoxyetanol.

Step (a2) can be optionally preceded by a filtration step.

Suitable organic solvents for diluting the solution obtained in step (a2) as described above include both hydrophilic and hydrophobic, polar and non-polar solvents. In a preferred embodiment, the organic solvents in step (a3) comprise ethyl acetate, acetone, N,N'-dimethylformamide, dimethylsulfoxide, methanol, ethanol, 2-methoxyethanol, 2-ethoxyethanol, 2-methoxypropanol, 1-methoxy-2-propanol, 2-ethoxypropanol, 1-ethoxy-2-propanol, n-propoxypropanol, 1-Methoxy-2-methyl-2-propanol, 1-propoxy-2-propanol, 2-propoxy-1-propanol, 2-(2-ethoxyethoxy)ethanol, 2-isopropanol, n-butanol, hexane, heptane, octane, or combinations thereof. As the presence of catalytic amounts of water molecules is mandatory, it is preferred to use solvents capable of dissolving at least minor amounts of water. In view of its low toxicity, ethanol is a preferred solvent.

Suitable aqueous bases for step (a4) as described above are those compounds which, when dissolved in water, generate an excess of OH$^-$ anions from water molecules, have the ability to form a bond with a proton, have an electron pair donor or a combination of the preceding. Examples of said aqueous bases are, but not limited to, NH$_3$ or aqueous solutions of NH$_3$, any amine (ammonia derived) compound of basic character such as aniline, pyridine, methylamine, trimethylamine or triethylamine, inorganic bases such as sodium hydroxide or potassium hydroxide. In a preferred embodiment, the aqueous base of step (a4) is selected from the group comprising ammonia, aniline, pyridine, triethylamine, sodium hydroxide, potassium hydroxide or combinations thereof. Not wishing to be bound by theory, it is believed that the OH-anions undergo a $S_N2$ nucleophilic attack at the metal atom of the calcium alkoxyalkoxide, forming the particles of the invention.

The step of ageing the solution, step (a5) involves putting the solution aside, stirred, optionally in the dark, for a given amount of time from 5 minutes to several days. Preferably, the ageing step is carried out from 1 to 24 hours, more preferably in 12 hours.

A third aspect of the invention relates to a calcium material, obtainable by the method of the second aspect of the invention, as well as by any combination of the above-mentioned method embodiments.

A fourth aspect of the invention is directed to a biocompatible matrix comprising the calcium material as defined in aspects one or three of the invention.

Therefore, the invention relates to the use of the calcium material of the invention in tissue regeneration and engineering applications. In a particular embodiment, said tissue is bone tissue or vascular tissue. In a preferred embodiment, said vascular tissue is involved in the wound healing process. In this specification, the term "tissue" is to be interpreted in the biology context, meaning that "tissue" refers to a cellular organizational level intermediate between cells and a complete organ. Generally, tissue may refer to any of connective, muscle, nervous and epithelial animal tissues.

Thus, in a fifth aspect, the invention relates to the calcium material of aspects one or three or to the biocompatible matrix of aspect four for use in tissue regeneration, preferably selected from the group consisting of wound healing, bone regeneration, skin regeneration, muscle regeneration, cardiac regeneration and promotion of vascularization. In the context of the present invention, non-limiting examples of tissue regeneration applications also include promotion of rapid vascularization phenomena.

As used herein, the term "biocompatible matrix" refers to the biocompatibility of a scaffold or matrix for tissue-engineering products. It refers to the ability of said scaffold or matrix to perform as a substrate that will support the appropriate cellular activity, including the facilitation of molecular and mechanical signalling systems, in order to optimise tissue regeneration, without eliciting any undesirable effects in those cells, or inducing any undesirable local or systemic responses in the eventual host. In the present case, the material is biodegradable. The material can also be metabolized.

The term "biodegradable" used herein is to be understood as referring to those materials which breakdown by the effect of the physiological environment.

The term "scaffold" in the present invention refers to a processed biomaterial that acts as a template and provides the necessary support for cell growth and differentiation in which new tissue can regenerate.

The invention also relates to the use of a biocompatible matrix comprising the calcium material as defined in aspects one and three of the invention, or by the combination of particular method embodiments of the present invention, in tissue regeneration. Preferably, said use is in wound healing processes and tissue engineering applications. Non-limiting examples of said tissue regeneration are bone regeneration, skin and hair regeneration, muscle regeneration, cardiac regeneration, rapid vascularization phenomena.

In a final aspect of the invention, the invention is directed to the use of the calcium material of aspects one or three or the biocompatible matrix of aspect four for the cosmetic regeneration of hair.

EXAMPLES

The present invention will now be described by way of examples which serve to illustrate the construction and testing of illustrative embodiments. However, it is understood that the present invention is not limited in any way to the examples below.

Example 1. Fabrication Method of Calcium 2-Methoxyethoxide Precursor Particles

Calcium 2-methoxyethoxide was synthesized by refluxing metal calcium (98%, Panreac) in anhydrous 2-methoxyethanol (99.8%, Sigma Aldrich) to reach 1M concentration. Briefly, 10.12 g of metallic calcium were put inside a 500 mL round-bottom flask. 200 mL of 2-methoxyethanol were added under Ar(g) atmosphere using a syringe. The mixture was then stirred at 134° C. under reflux for 24 hours to dissolve the metallic calcium. The solution was then filtered using a 450 μm pore filter. The solution was taken to 250 mL adding 2-methoxyethanol and using a 250 mL volumetric flask. The solution was placed under Ar(g) atmosphere in a gas tight 250 mL glass vial and stored at −20° C. for a maximum of 6 months.

10 mL of the previous calcium 2-methoxyethoxide (1M) solution were diluted with 90 mL of absolute ethanol (99.5%, PanReac) in a 250 mL round-bottom flask. Additionally about 30 mL of ammonia (30%, PanReac) were added under stirring. The solution was aged overnight at room temperature under stirring. Then, it was centrifuged at 20000 rpm for 20 minutes to collect the precipitated particles. The particles were washed twice with absolute ethanol and centrifuged a second time at 20,000 rpm for 20 minutes. A last wash was performed with hexane and again the particles were centrifuged at 20000 rpm for 20 minutes. Drying the centrifuged particles at 70° C. for 2 hours yields sample Ca70. The yield is about 700-800 mg of nanoparticles for the volumes previously mentioned.

Example 2. Fabrication Method of the Controllable Release, Calcium Material of the Invention The calcium 2-methoxyethoxide particles obtained by the fabrication method of example 1 were firstly ground and then treated in an oven/muffle furnace at the conditions given in the following table, leading to the samples Ca100, Ca200, Ca 300, Ca400 and Ca500.

| Sample ID | Temperature | Heating time (total) |
| --- | --- | --- |
| Ca100 | 100° C. | 12 hours |
| Ca200 | 200° C. | 12 hours |
| Ca300 | 300° C. | 12 hours |
| Ca400 | 400° C. | 12 hours |
| Ca500 | 500° C. | 12 hours |

Example 3. Energy Dispersive Spectroscopy Measurements

Samples were prepared for EDS by coating them with a thin layer of carbon.

The obtained calcium material of the present invention comprises a mixture of at least one calcium alkoxyalkoxide precursor, calcium hydroxide and calcium carbonate at different molar ratios. The ratio of such components may vary with the temperature treatment, due to the incomplete decomposition of the organic material and/or incomplete $CO_2$ incorporation into $Ca(OH)_2$. Energy Dispersive Spectroscopy (EDS) experiments on samples obtained in example 2 (calcium 2-methoxyethoxide) show that all of the controllable release calcium material samples of example 2 comprise Ca, O and C. An illustrative example is found in FIG. 1, where the EDS spectrum of sample Ca400 shows the presence of elements Ca, O and C.

Example 4. X-Ray Powder Diffraction Characterisation of the Calcium Material The samples of example 2 (calcium 2-methoxyethoxide) were prepared for X-ray powder diffraction (XRD, PANalytical, Bragg-Brentano, CuKα=0.15406 nm) by manual pressing of some of the powder materials, by means of a glass plate to get a flat surface, in cylindrical standard sample holders of 16 millimetres of diameter and 2.5 millimetres of height. Samples were analysed using a PANalytical X'Pert PRO MPD Alpha1 Powder Diffractometer in Bragg-Brentano θ/2θ geometry of 240 millimetres of radius.

Figure 2A:
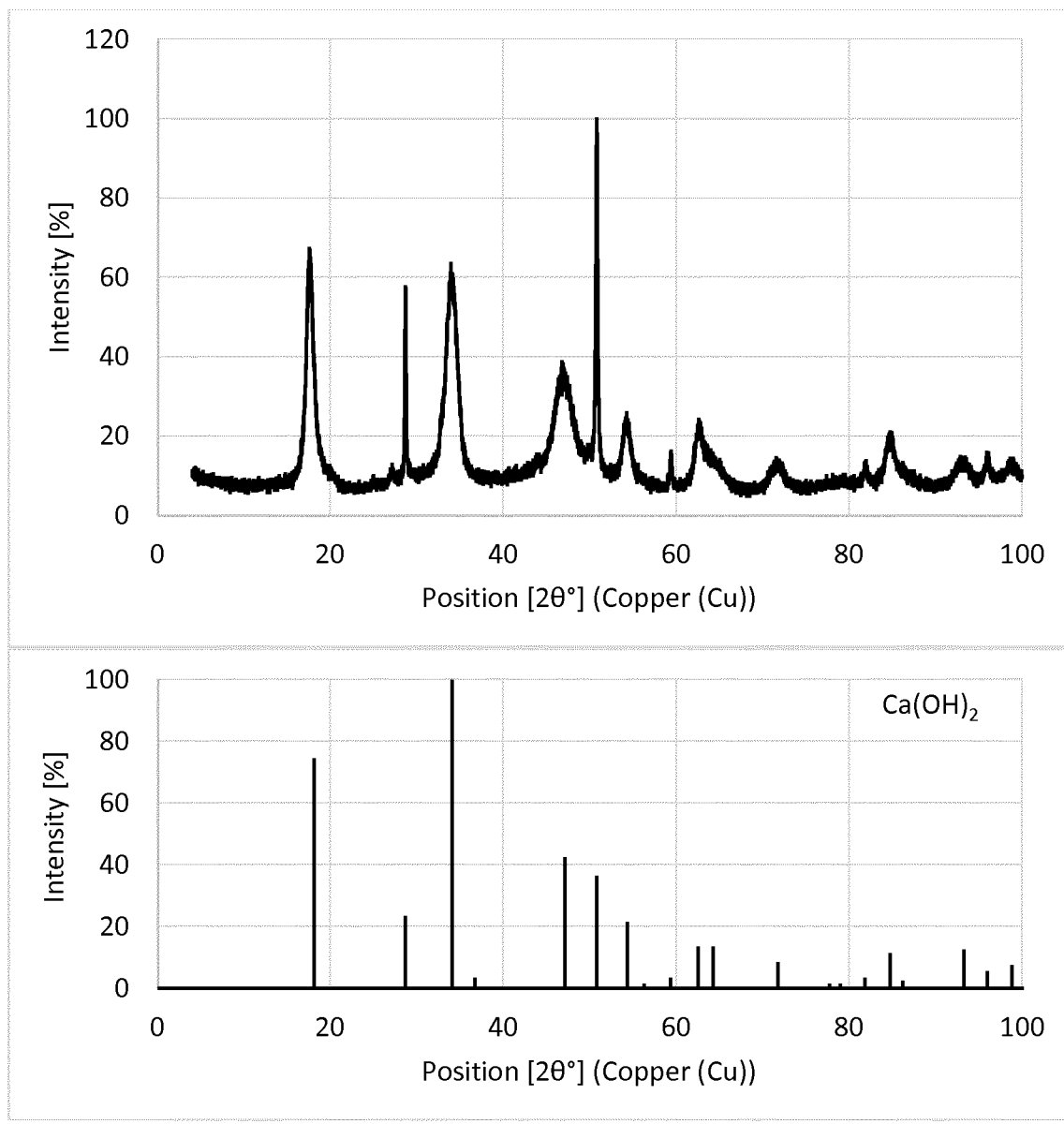
FIG. 2: X-ray diffractograms of samples Ca100 (FIG. 2A); Ca300 (FIG. 2B) and Ca500 (FIG. 2C) as well as comparative diffractograms of $Ca(OH)_2$, $Ca(OH)_2$ and $CaCO_3$, and $CaCO_3$ and CaO, in FIGS. 2A, 2B and 2C, respectively.
Figure 2B:
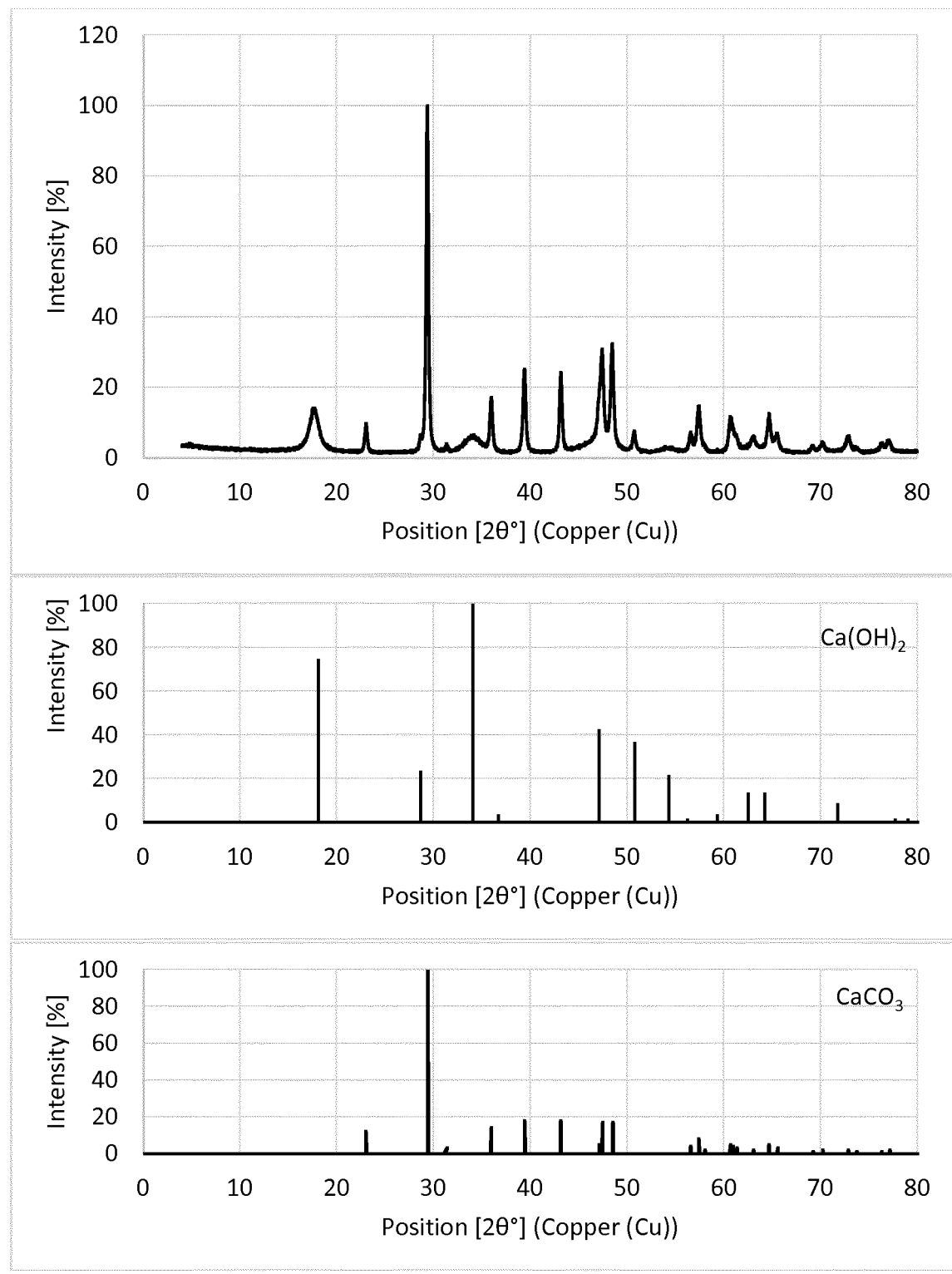
Figure 2C:
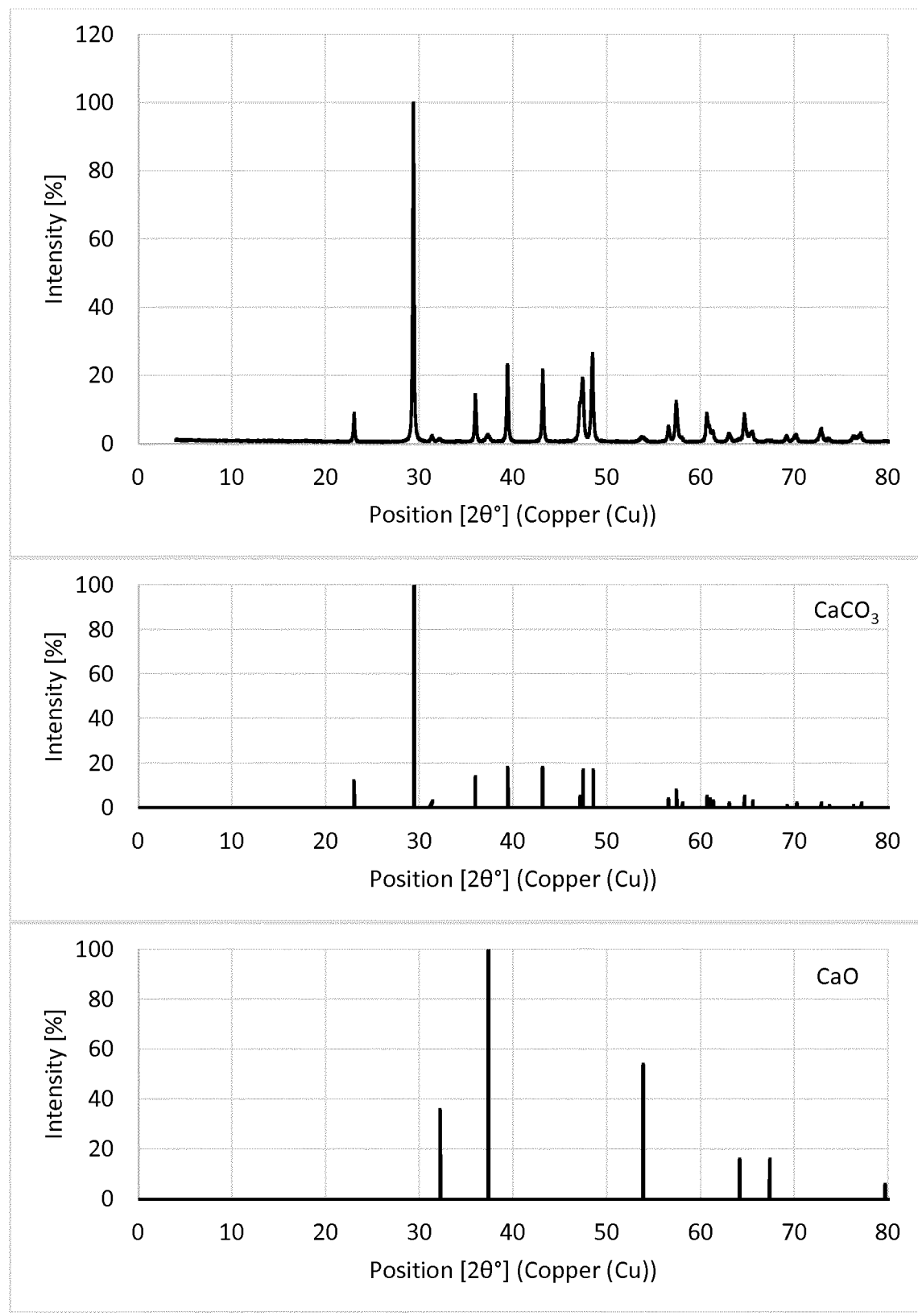

FIGS. 2A, 2B and 2C show the X-ray diffractograms of samples Ca100, Ca300 and Ca500, respectively from example 2 (calcium 2-methoxyethoxide precursor). X-ray powder diffraction experiments on the samples of example 2 showed higher crystallinity on higher thermal treatments. While the XRD profile of sample Ca100 shows a pattern which resembles that of pure $Ca(OH)_2$, the XRD profile for sample Ca300 is associated with a pattern matching a weight ratio of 65:35 $Ca(OH)_2:CaCO_3$. Increasing the temperature treatment to 500° C. leads to obtaining sample Ca500, which is characterised by an XRD pattern resembling that of $CaCO_3$. It is thus observed that the final composition of the calcium material evolves with the temperature treatment (due possibly to organic material calcination and $CO_2$ incorporation), which ultimately affects the calcium release profile, as shown below in example 7.

Example 5. Elemental Analysis of the Calcium Material

Total carbon content (TCC) and total organic carbon (TOC) percentage values were obtained by measuring $CO_2$ values via combustion elemental analysis using an Elemental Analyzer EA CE 1108 equipment (Thermo Fisher Scientific) under standard conditions. The combustion was achieved by applying an oxidation temperature of 1060° C. A mixture of vanadium pentoxide and tin powder were used as additives for the combustion. Atropine was used as reference.

In the case of total organic carbon measurements, all samples (from examples 1 and 2, calcium 2-methoxyethoxide) were firstly submitted to a treatment aiming at removing all inorganic carbon, in order to eliminate carbonates via $CO_2$ formation prior to combustion considering the total inorganic carbon. This was achieved by treating the samples with HCl 6N in Ag capsules.

Figure 3:
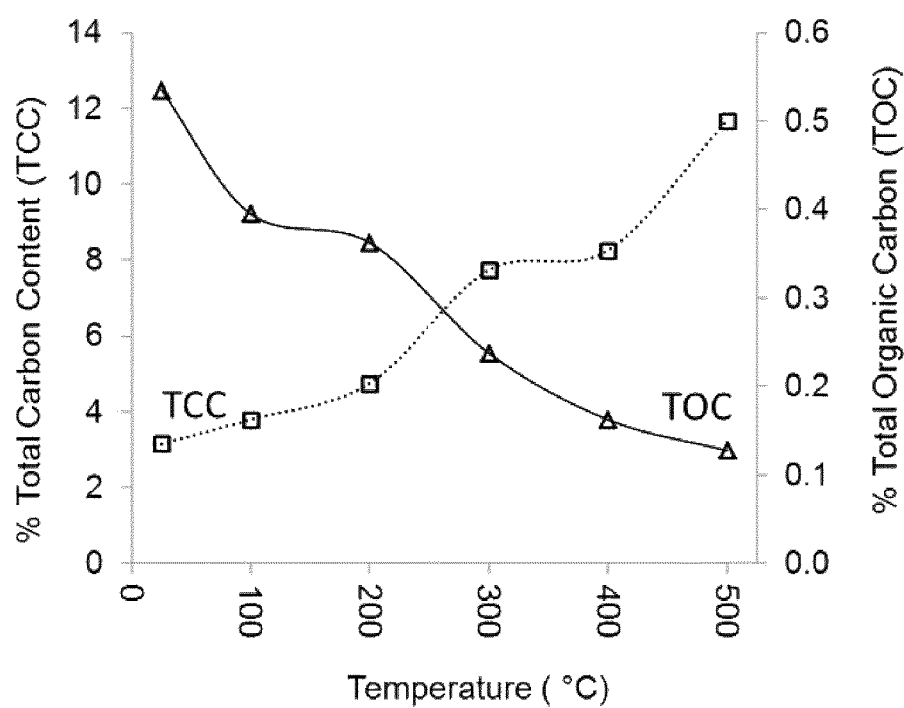
FIG. 3: Total Organic Carbon (TOC, Δ) and Total Carbon Content (TCC, □) as a function of the temperature treatment (samples Ca100, Ca200, Ca300, Ca400 and Ca500) obtained by means of elemental analysis.

The TCC and TOC values obtained from elemental analysis for the samples prepared in examples 1 and 2 are summarized in the following table and shown in FIG. 3, which clearly shows that a manifold of compositions is obtainable by tuning the temperature treatment.

| Sample ID | Temperature | TOC/% | TCC/% |
| --- | --- | --- | --- |
| Ca70 | 70° C. (for 2 hrs)[a] | 0.54 | 3.15 |
| Ca100 | 100° C. (for 12 hrs) | 0.40 | 3.80 |
| Ca200 | 200° C. (for 12 hrs) | 0.36 | 4.75 |
| Ca300 | 300° C. (for 12 hrs) | 0.24 | 7.74 |
| Ca400 | 400° C. (for 12 hrs) | 0.16 | 8.26 |
| Ca500 | 500° C. (for 12 hrs) | 0.13 | 11.68 |

[a]For sample Ca70 it is assumed that drying at 70° C. for 2 hours is insufficient to modify the chemical structure of the sample.

Results are displayed as mass percentage (mass of measured TCC or mass of measured TOC divided by the total mass of the sample, multiplied by 100).

Figure 5A:
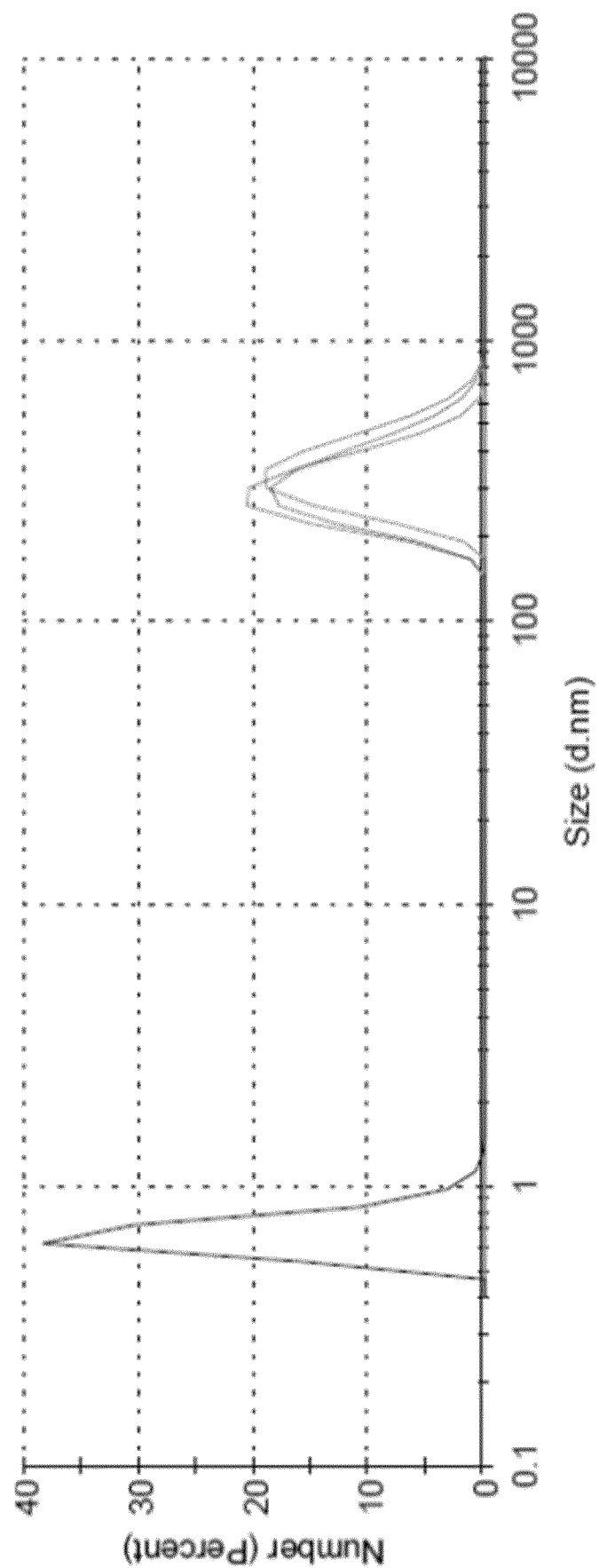
FIG. 5A: Dynamic Light Scattering (DLS) results of sample Ca400.
Figure 5B:
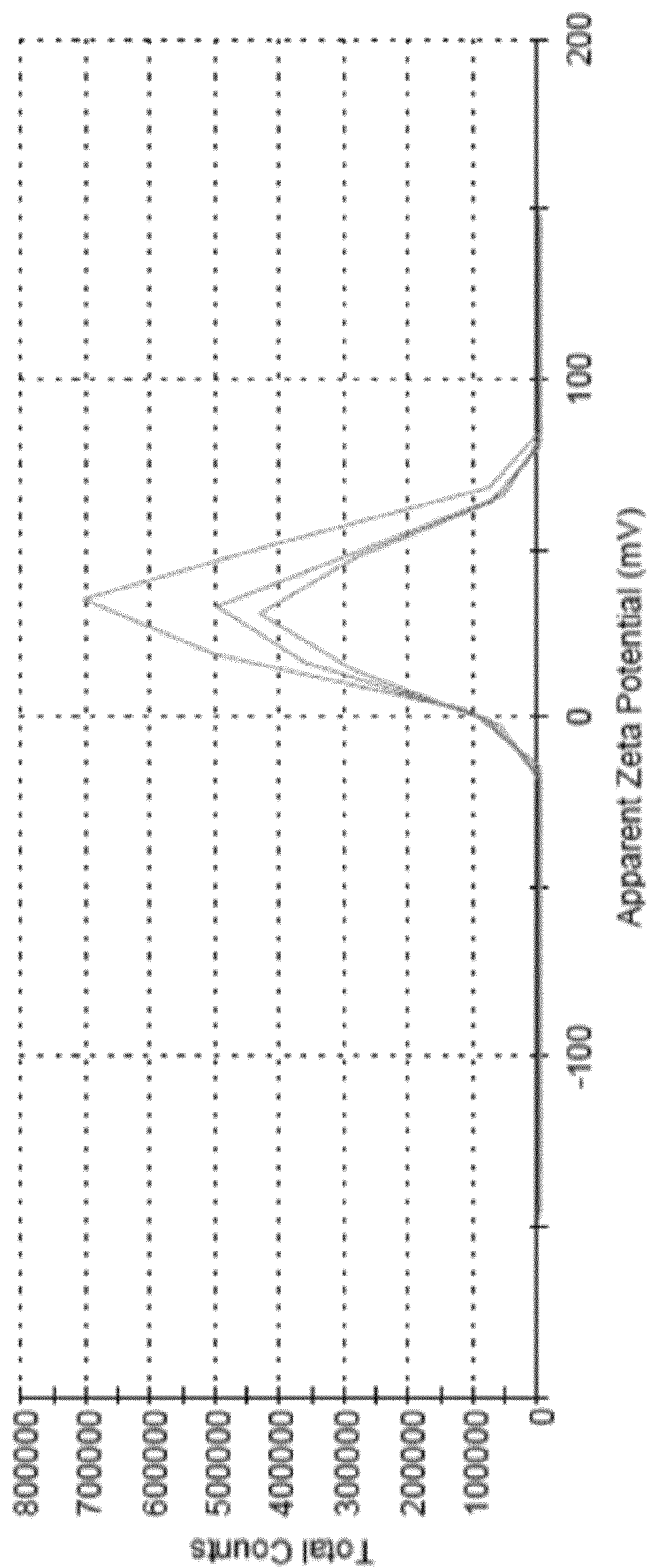
FIG. 5B: Zeta-potential analysis of sample Ca400.

Example 6. Characterisation of the Controllable Release, Calcium Material by DLS and Z-Potential Dynamic Light Scattering (DLS) studies on sample Ca400 prepared in Example 2 revealed that the nanoparticle size is around 324.1±103.9 nm and that its Z-potential value is around 30.6±16.3 mV, as shown in FIGS. 5A and 5B, respectively.

Example 7. Cumulative $Ca^{2+}$ Release

The samples of Example 2 (calcium 2-methoxyethoxide) were ground and each resulting sample powder was suspended in 10 mL of purified milli-Q water at 1 mg/mL in 15 mL tubes. For each sample three replicas were prepared. Tubes were kept at 37° C. with soft agitation.

Each data point corresponding to a given time corresponds to the same ground powder sample being exposed to gentle agitation at 37° C. for an increasing amount of time. In detail, after a given agitation time (1 h, 5 h, 21 h, 45 h, 69 h, 94 h and 120 h), samples were centrifuged at 4500 rpm for 6 minutes and 1 mL of the supernatant was diluted in 9 mL of $HNO_3$ 0.6% (v/v) and stored at 4° C. for ICP analysis (ICP-OES PerkinElmer, Optima 3200 RL model, standard conditions). After collecting the 1 mL aliquot, the remainder supernatant of the centrifuged sample was renewed for all samples. For this purpose, after the centrifugation step, the supernatant volume was carefully removed until 1 mL of the supernatant's solvent was left to avoid removing particles. New fresh purified milli-Q water was added until reaching the initial volume of 10 mL. The deposited powder was re-suspended by gently shaking of the tubes, which were stored at 37° C. with soft agitation for further exposition of the powders to water.

Figure 4A:
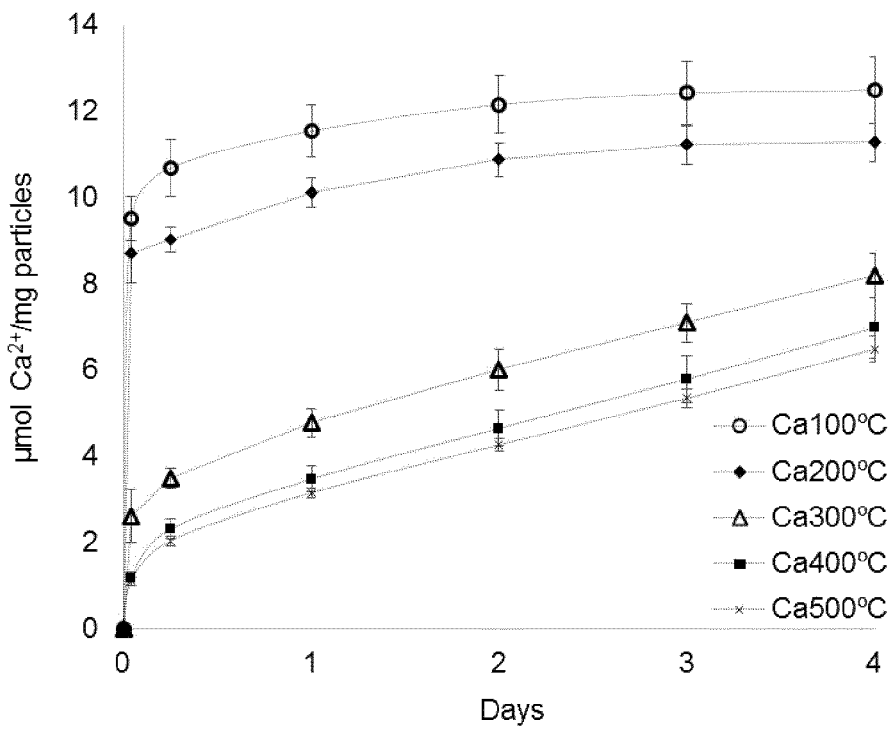
FIG. 4A: Cumulative $Ca^{2+}$ release (μm of $Ca^{2+}$ per mg of sample) for samples Ca100 (○), Ca200 (♦), Ca300 (Δ), Ca400 (■) and Ca500 (x) as a function of immersion time, up to 4 days. Error bars represent the variability of the data obtained from three replicas.
Figure 4B:
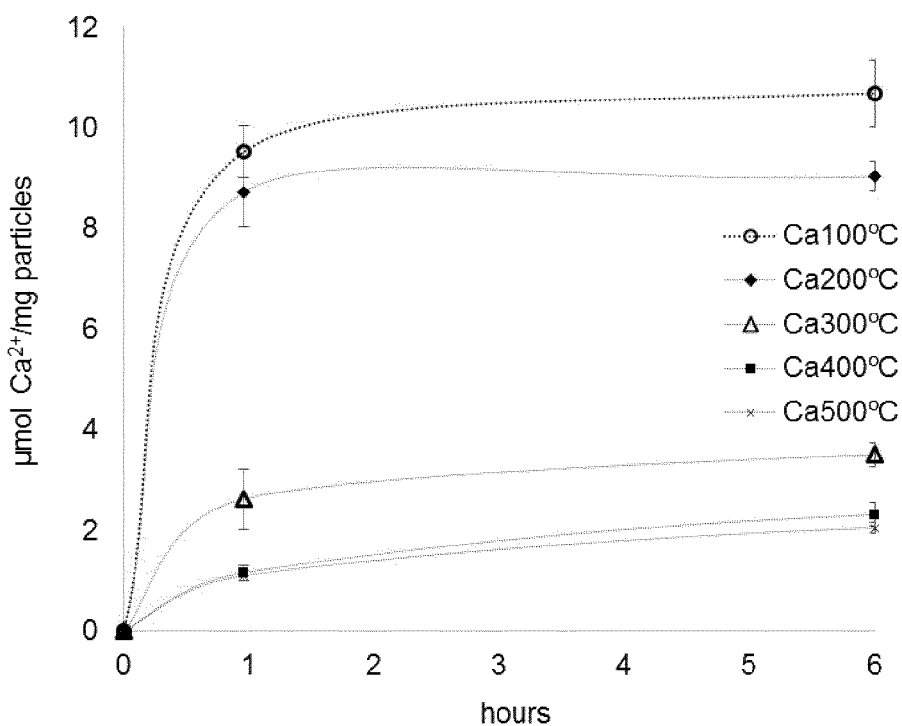
FIG. 4B: Cumulative $Ca^{2+}$ release (μm of $Ca^{2+}$ per mg of sample) for samples Ca100 (○), Ca200 (|), Ca300 (Δ), Ca400 (□) and Ca500 (x) as a function of immersion time, for the first 6 hours of the experiment. Error bars represent the variability of the data obtained from three replicas.

Inductively Coupled Plasma Mass Spectrometry (ICP-MS) studies provided the data for the amount of released calcium as a function of time, an indication of the release rate for the samples described above, which is represented in FIGS. 4A and 4B. Surprisingly, the analysis revealed that the higher the temperature in the thermal treatment of the particles, the slower the $Ca^{2+}$ release. The results also show a clear $Ca^{2+}$ release trend below and above 200° C. At temperature treatments of 100° C. or 200° C., samples show intense initial release rates (initial bursts of 9.5 µmol of $Ca^{2+}$ per mg of calcium material in just 1 hour) of calcium ions which rapidly deplete the releasable calcium as after 2 days there is no significant increase in the cumulative calcium ions release. Such a profile can be important for applications requiring intense initial calcium concentrations such as rapid vascularization, increase the pH value for antitumor applications (Nanoscale, 2016, 8, 12639) or drug release (Z. Dong et al., Biomaterials, 2016, 110, 60-70). At higher treatment temperatures, the measured release rate of the prepared samples shows a much slower initial release rate (1.1 µmol of $Ca^{2+}$ per mg of calcium material in the first hour) and a steady release rate that spans further in time (6.5 µmol of $Ca^{2+}$ per mg of calcium material) and stays stable even after 4 days. Noticeably, the total amount of released calcium ions from the Ca500 sample upon 4 days of immersion is still largely inferior to the initially released $Ca^{2+}$ ions for the Ca100 sample after 1 hour of immersion.

Example 8. Biomaterial Comprising the Calcium Material of the Invention

The following procedure is general and can be applied to any of the materials of the invention. As a particular example, the nanoparticles of Example 2 were dispersed in a polylactic acid (PLA) matrix of a composition of 70% by weight isomer L and 30% by weight copolymer including the two isomers using 2,2,2-trifluoroethanol as solvent and an ultrasonic couple as mechanical disperser. The resulting dispersion contained about 4% polylactic acid and 1% glass nanoparticles by weight. The slurry can be coupled into an infusion pump and connected to a high voltage power source. Usual experimental parameters are 1 mL/h flow, 10 kV, 15 cm tip-to-collector distance and a rotary mandrel running at 100 rpm in order to obtain random nanometric sized PLA fibers. In vitro experiments with osteoclasts showed good adhesion, as well as for in vivo experiments with chick embryo chorioallantoic membrane (CAM) models and mice for wound healing, showing an improvement in vascularization and wound reduction respectively.

Example 9. Comparative Calcium Material

Comparative calcium material of formula P:Ca 3:7 (numbers refer to the used volume of P and Ca precursors respectively) was prepared according to the following procedure.

Ethylphosphate was synthesized by refluxing metal phosphorus pentoxide (98%, Panreac) in anhydrous 2-methoxyethanol (≥99.99%, Sigma Aldrich) to reach 4M concentration. Briefly, 28.39 g of phosphorus pentoxide were put inside a 500 mL round-bottom flask under Ar(g) atmosphere. 80 mL of distilled absolute ethanol (99.5%, PanReac) were added using a syringe and keeping the bottom flask in an ice bath. The mixture was then stirred at 84° C. under reflux for 12 hours to dissolve the phosphorus pentoxide. The solution was then filtered using a 450 µm pore filter. The solution was taken to 100 mL adding distilled absolute ethanol and using a 100 mL volumetric flask. The solution was placed under Ar(g) atmosphere in a gas tight 100 mL glass vial and stored at −20° C. for a maximum of 6 months.

7 mL of the calcium methoxyethoxide (1M) solution prepared according to Example 1 and 3 mL of ethyl phosphate (4M) solutions were diluted with 90 mL of absolute ethanol (99.5%, PanReac) in a 250 mL round-bottom flask. Additionally, approximately 30 mL of ammonia (30%, PanReac) were added under stirring. The solution was aged overnight at room temperature under stirring. Then, it was centrifuged at 20000 rpm for 20 minutes to collect the precipitated particles. The particles were washed twice with absolute ethanol and centrifuged a second time at 20,000 rpm for 20 minutes. A last wash was performed with hexane and again the particles were centrifuged at 20000 rpm for 20 minutes. Drying the centrifuged particles at 70° C. for 2 hours yields comparative sample P:Ca. The yield is about 700-800 mg of nanoparticles for the volumes previously mentioned.

Figure 6:
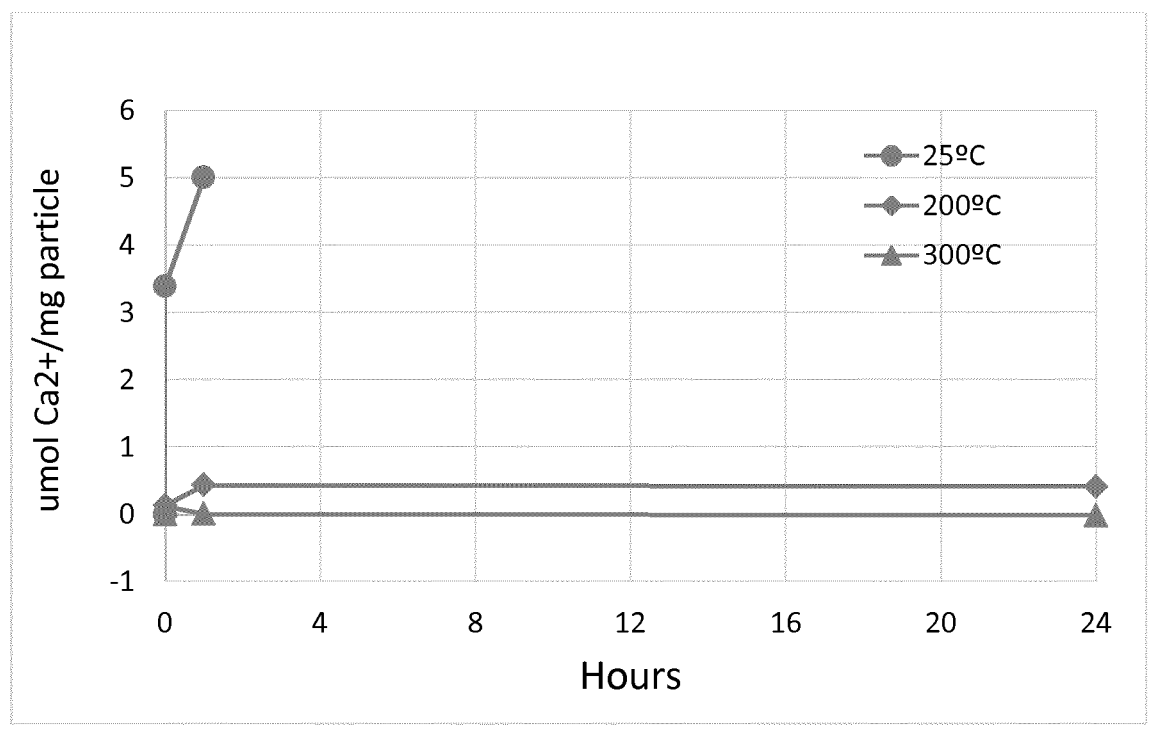
FIG. 6: Cumulative $Ca^{2+}$ release (μm of $Ca^{2+}$ per mg of sample) for comparative phosphate glass nanoparticles (atomic ratio P:Ca 6:7)) for samples treated at 25° C. (●), 200° C. (♦) and 300° C. (▲) as a function of immersion time, for the first 24 hours of the experiment.

The comparative material P:Ca was submitted to the thermal treatment of Example 2 (at temperatures of 25° C. (●), 200° C. (♦) and 300° C. (▲), and the cumulative calcium release measured as in Example 7. Results in FIG. 6 show that the particles lack controllable release of calcium since they either release all calcium in an initial burst (25° C.) or do not release any calcium at all (200° C. and 300° C.).

Example 10. Fabrication Method of Other Calcium Alkoxyalkoxides Precursor Particles The material of the present invention was also prepared starting from other precursor alkoxyalkoxides. To prepare said precursor particles, corresponding alkoxyalcohols were subjected to the procedure described in example 1, except when indicated otherwise.

| Sample ID | Alkoxyalkoxide ligand | Alkoxyalcohol | Reflux time |
| --- | --- | --- | --- |
| Ca400-1 | 1,3-diethoxy-2-propoxide | 1,3-diethoxy-2-propanol | 24 hours |
| Ca400-2 | 2-ethoxyethoxide | 2-ethoxyethanol | 24 hours |
| Ca400-3 | 1-ethoxy-2-propoxide | 1-ethoxy-2-propanol | 48 hours |

Example 11. Fabrication Method of the Controllable Release Calcium Material of the Invention Starting from Other Precursors The particles obtained in example 10 (Ca400-1, Ca400-2 and Ca400-3) were subjected to the same heating procedure as the one described in example 2, except that in the present example the samples were only submitted to a temperature of 400° C.

Figure 7:
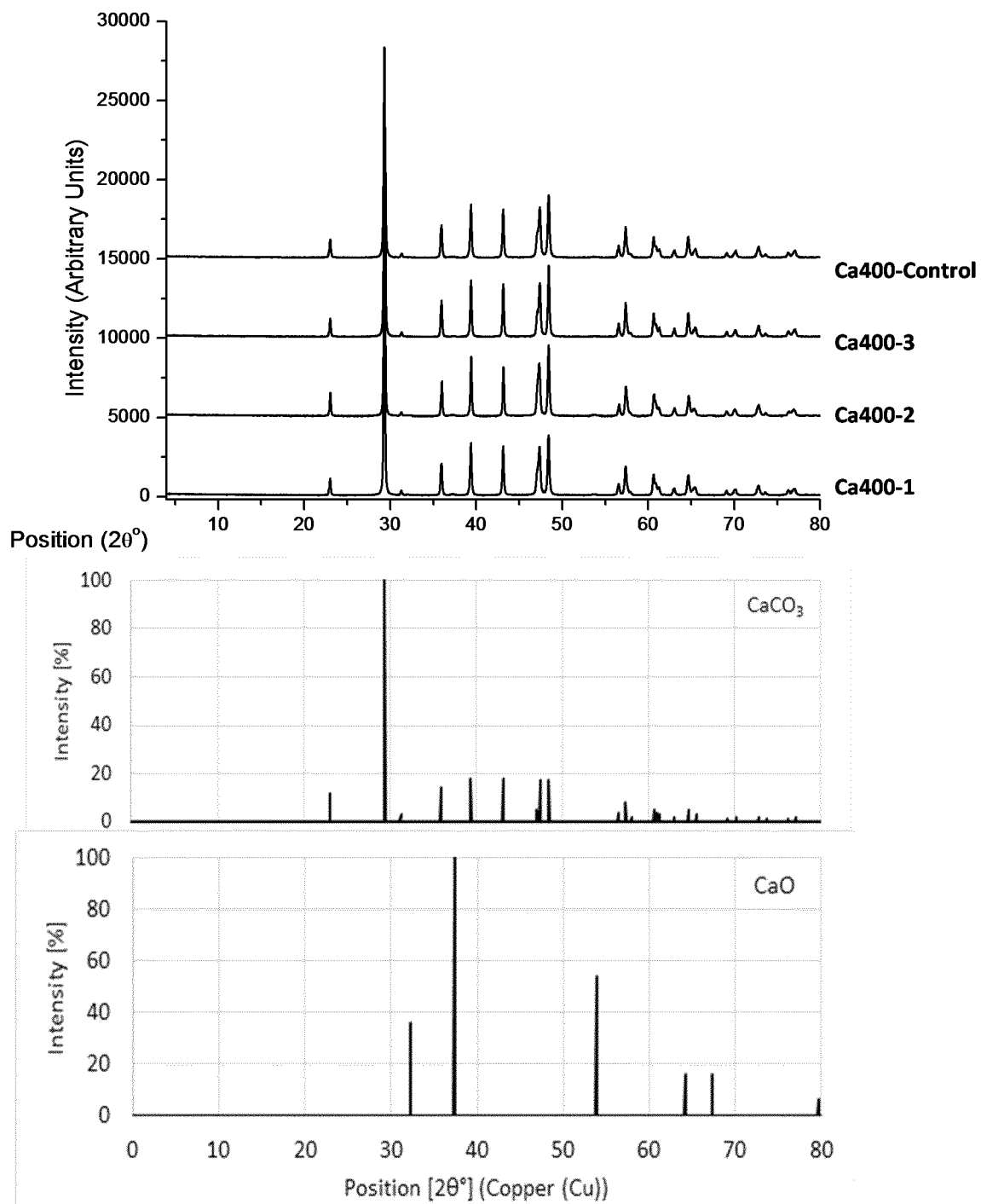
FIG. 7: X-ray diffractograms of samples Ca400 (Ca400-control), Ca400-1, Ca400-2 and Ca400-3 as well as comparative diffractograms of $CaCO_3$ and CaO.

Results in FIG. 7 show the X-ray diffractograms of the samples prepared in example 10, following the same protocol as described in example 4. The data shown proves that a similar product is obtained independently of the precursor.

Example 12. Characterisation of the Controllable Release, Calcium Material Obtained from 1,3-Diethoxy-2-Propoxide, 2-Ethoxyethoxide and 1-Ethoxy-2-Propoxide by SEM and Z-Potential Scanning Electron Microscopy images, Dynamic Light Scattering and Z-potential measurements of samples Ca400 (example 2) and Ca400-1 Ca400-2 and Ca400-3 prepared in Example 11 are summarized in the table below.

| Sample ID | Alkoxyalkoxide | Size/nm (FE-SEM) | ζ-potential ± STD/mV |
|---|---|---|---|
| Ca400 | 2-methoxyethoxide | 84.5-149.5 | 25.3 ± 24.6 |
| Ca400-1 | 1,3-diethoxy-2-propoxide | 89.9-118.6 | 44.2 ± 15.3 |
| Ca400-2 | 2-ethoxyethoxide | 50.8-70.0 | 48.1 ± 22.2 |
| Ca400-3 | 1-ethoxy-2-propoxide | 59.0-134.5 | 35.9 ± 14.4 |

Figure 8:
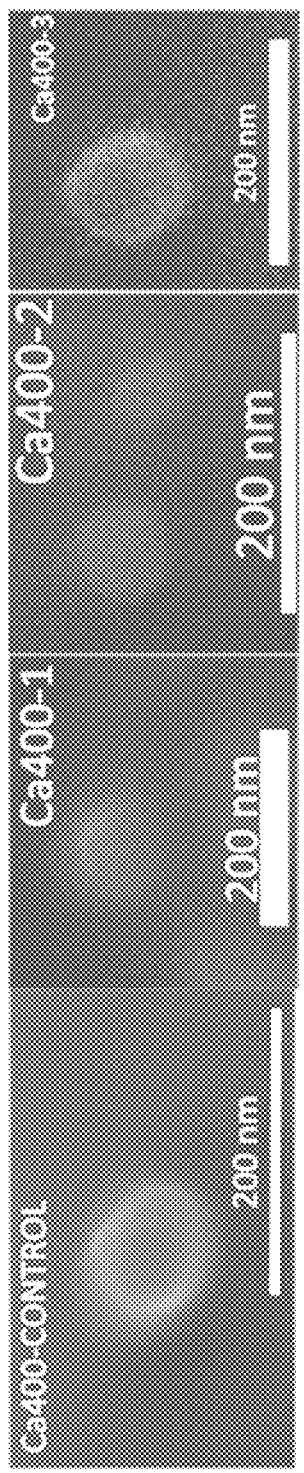
FIG. 8: FE-SEM images of dispersed nanoparticles of precursor particles Ca400, Ca400-1, Ca400-2 and Ca400-3.

FIG. 8 shows the SEM images of the four samples.

Example 13. Cumulative $Ca^{2+}$ Release from Other Precursors

The samples of Example 11 (obtained from calcium 1,3-diethoxy-2-propoxide, 2-ethoxyethoxide and 1-ethoxy-2-propoxide) were tested following the same procedure as the one described in example 7.

Figure 9:
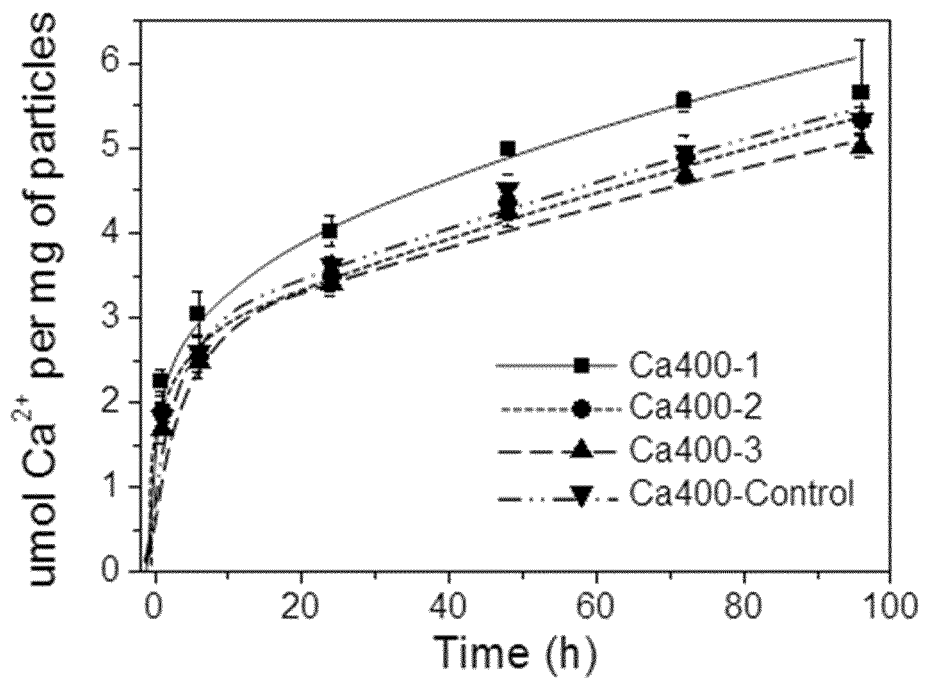
FIG. 9: Cumulative $Ca^{2+}$ release (μm of $Ca^{2+}$ per mg of sample) for samples Ca400, Ca400-1, Ca400-2 and Ca400-3 as a function of immersion time. Error bars represent the variability of the data obtained from three replicas.

Inductively Coupled Plasma Mass Spectrometry (ICP-MS) studies provided the data for the amount of released calcium as a function of time, an indication of the release rate for the samples described above, which is represented in FIG. 9. The results show similar behaviour as the one obtained for the control, Ca400 sample of example 2.

Example 14. Effect of Ca400 Particles (Calcium 2-Methoxyethoxy) on Skin Wound Healing The aim of this study was to assess the wound healing capacity of sample Ca400 for skin regeneration in a model of obese and diabetic mice with a mutation in the leptin receptor (db/db). Specifically, to assess the activity of the particle-based biomaterials of the present invention in improving the wound healing of skin lesions induced in diabetic mice and to study neovascularization of the regenerated tissue.

Animal Model. Eight Obese and Diabetic Mice with a Mutation in the Leptin Receptor, known as db/db, were obtained from Charles River Laboratory and used at 8-weeks old. To avoid hormone interference in the healing of wounds, male mice were used.

Generation of a Pressure Ulcer Wound.

To generate pressure ulcers on the dorsal side of mice a previously reported model was used that consisted in performing cycles of ischemia-reperfusion (IR) with the external application of two magnets (Stadler et al., 2004; Saito et al., 2008; Wassermann et al., 2009). This process produces two circular ulcers covered by necrotic tissue separated by a bridge of healthy skin.

Dressing Application.

Ca400 particles as described in example 2 were electro-spun with polylactic acid (PLA) nanofibers, cut into squares and applied into the wounds. A commercial neutral wound dressing was used as control dressings. Dressings were covered with adhesive Plaster (Coverplast® Latex-free, BSNmedical) and secured with elastic gauze (Genové Dermatologics). Dressings were changed every 24 h. Mice were sacrificed by cervical dislocation under anesthesia. The wounds were excised leaving 2 mm of margin, cut in half and fixed in 10% neutral buffered formalin solution for 24 h for histological analysis.

Wound imaging. At day 0 and before every dressing replacement, wounds were photographed with a Mavica FD91 digital camera (Sony, Minato, Tokyo, Japan) and the ORCA-2BT Imaging System (Hamamatsu Photonics, Hamamatsu, Japan) provided with a C4742-98-LWG-MOD camera fitted with 512×512-pixel charge-couple device (CCD) cooled at −80° C. Wound area from the images was quantified using the Wasabi image analysis software (Hamamatsu Photonics) and normalized for the wound area at day 0.

CD31 staining and analysis. Histological changes were evaluated in the full dermis and hypodermis. In each sample four regions of interest—ROI—(non-lesioned dermis, lesioned dermis, non-lesioned hypodermis, and lesioned hypodermis) were selected manually in each tissue sections.

Formalin-fixed wounded skin tissues were embedded in paraffin, cut at 4-5 μm and stained with anti-CD31 antibody (ab28364) or the corresponding isotype control (ab27478) for the negative control. CD31 antibody was used as a marker of endothelial cells to quantify the area of blood vessels. Vessels were defined as CD31 positive labeling. Negative samples stained with the isotype control were negative (data not shown).

Full images of CD31 immunostained sections were acquired by a NanoZoomer-2.0 HT C9600 scanner (Hamamatsu) at 20× magnification, in which 1 pixel corresponds to 0.46 um. QuPAth software was used to perform image analysis. The Positive pixel count algorithm in which pixels of image are segmented in positive (CD31 labelled—DABb positive pixels) or negative (DAB negative pixels—haematoxylin) were used with the following values:

Downsample factor=1.0

Gaussian sigma: 1

For the dermis, results are the percentage of the positive pixel following the equation:

positive DAB pixel %=number DAB positive pixels*100/(DAB positive pixels+DAB negative pixels).

White areas (tissue artefact/background) were not included.

Results

Figure 10:
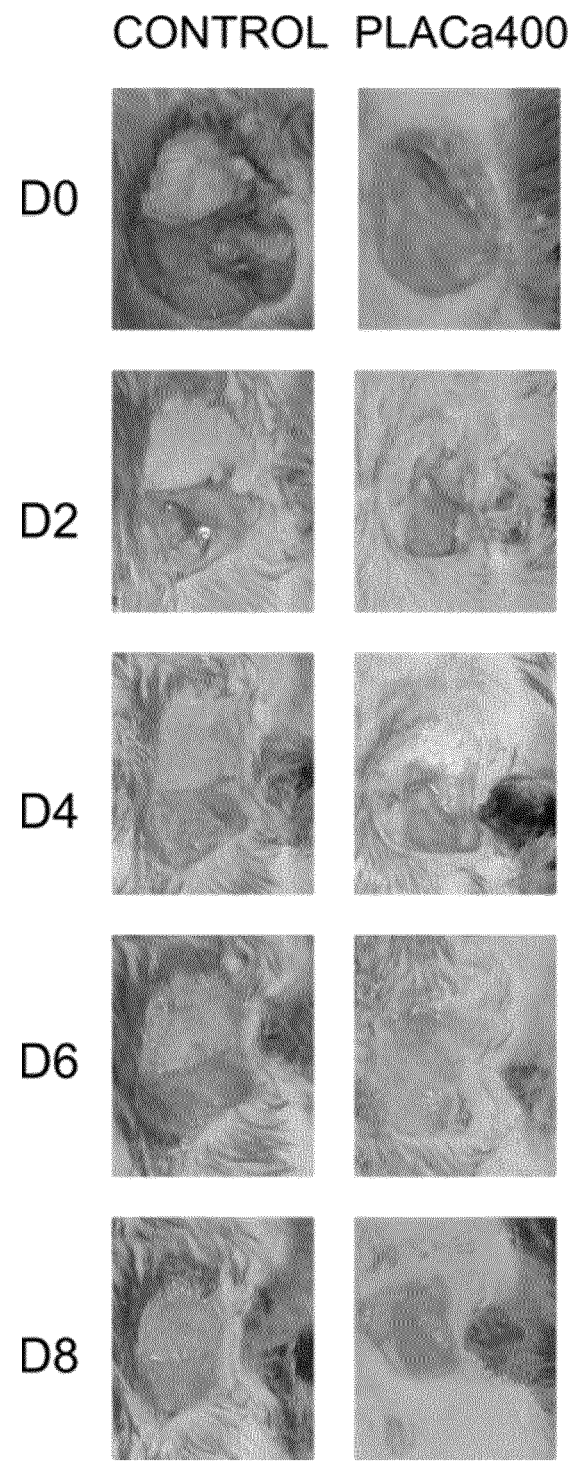
FIG. 10: Assessment of wound healing area at different time points. Representative images of the group treated with commercial dressing and PLA-Ca400 on day 0, 2, 4, 6 and 8 post-treatment.
Figure 11:
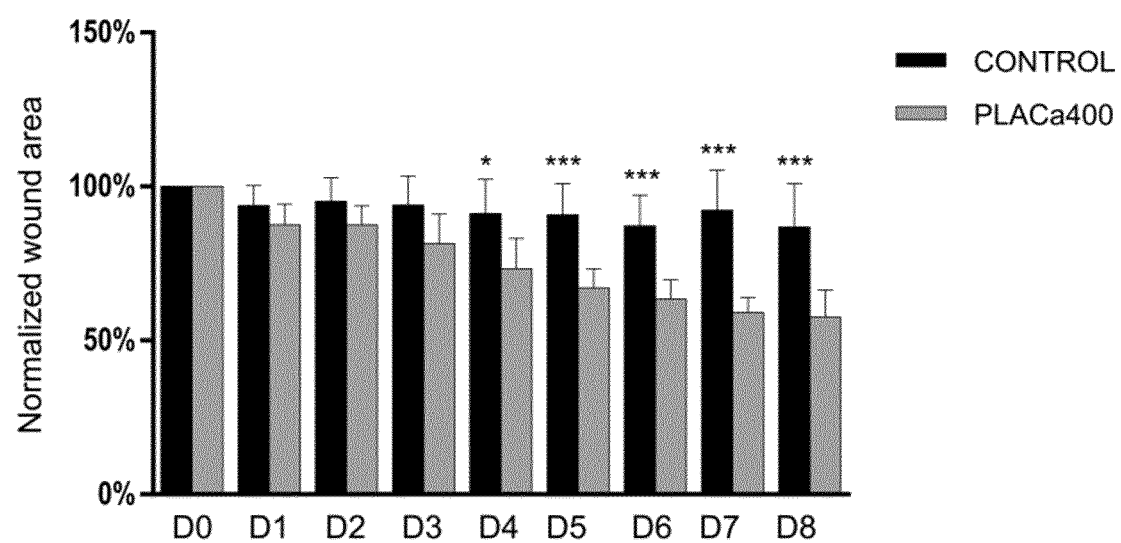
FIG. 11: Assessment of wound healing area at different time points at day 0, 1, 2, 3, 4, 5, 6, 7 and 8. Percentage of wound size relative to the initial size during the course of the experiment. Data is expressed as the mean±SD (n=8). *p<0.05 (vs PLA-Ca400),***p<0.0001 (vs PLA-Ca400).
Figure 12:
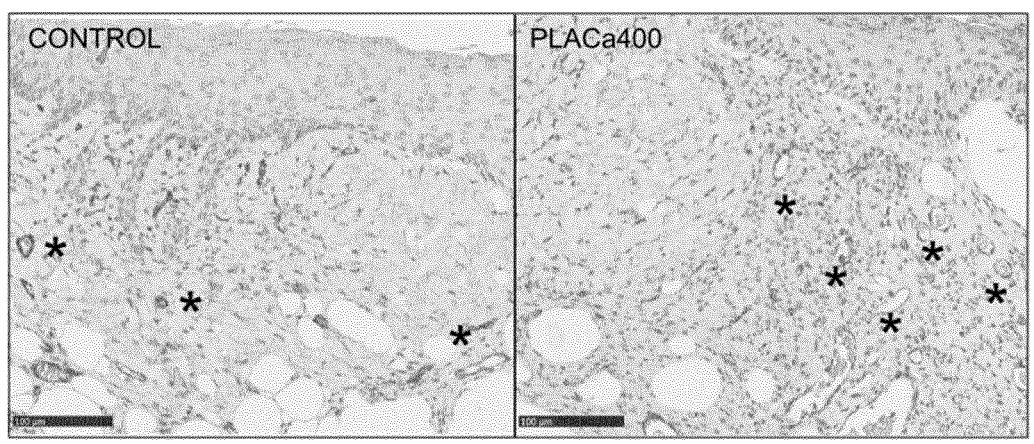
FIG. 12: Imaging and quantification of blood vessels immunolabelled for CD31. A) Representative images of immunostaining against CD31 of sections of wounds treated with commercial dressing and PLA-Ca400 8 days post-wounding. B) Quantification of the number of vessels from the immunostained images. *p<0.05 (vs. PLA-Ca400).
Figure 12:
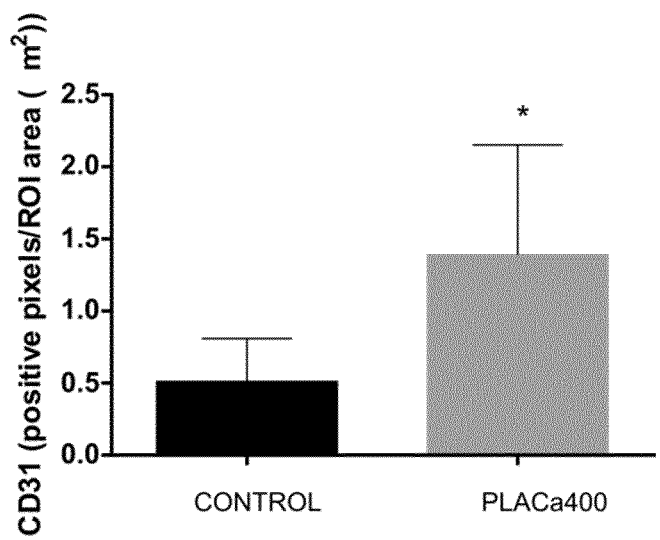

Quantification of the wound area showed a significant reduction over time in wounds treated with PLACa400 dressings. Wounds treated with the commercial dressing did not show any reduction in the wound area. Statistical analysis in the wound area indicates a significant decrease in wound area in wounds treated with PLACa400 compared to commercial dressing treatment (FIGS. 10 and 11). Tissue sections of wounds treated with PLA-Ca400 presented higher percentage of CD31 positive labelling when compared to commercial dressing-treated tissue sections (FIG. 12).

Ca400-based dressings promote the healing of ischemic wounds in an in vivo model of diabetic mice. Furthermore, Ca400 promoted increased vascularization which can be responsible for the improved healing of wounds.

The invention claimed is:

1. A biodegradable calcium material, of general formula (I):

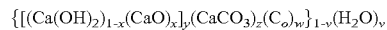

wherein $0 \leq x \leq 1$, $0.06 \leq y \leq 0.75$, $0.14 \leq z \leq 0.93$, $0.01 \leq w \leq 0.11$, $0 \leq v \leq 0.44$ and $C_o$ designates a carbon containing fraction comprising one or more compounds selected from the group consisting of calcium alkoxyalkoxide, alkoxyalcohol, alcohol, calcium alkoxide, graphite and combinations thereof, wherein the alkoxyalkoxide in the calcium alkoxyalkoxide is an alkoxyalkoxide of general formula $R_1OAO^-$, wherein A is a divalent, optionally substituted, linear or branched $C_1$-$C_6$ alkyl chain and $R_1$ is a linear $C_1$-$C_6$ alkyl chain or $C_6$-$C_{12}$ aryl;

the alkoxyalcohol is an alkoxyalcohol of general formula $R_1OAOH$, wherein A is a divalent, optionally substituted, linear or branched $C_1$-$C_6$ alkyl chain and $R_1$ is a linear $C_1$-$C_6$ alkyl chain or $C_6$-$C_{12}$ aryl;

the alcohol is linear or branched, optionally substituted, $C_1$-$C_6$ alkyl alcohol or $C_6$-$C_{12}$ aryl alcohol and the calcium alkoxide is linear or branched, optionally substituted, $C_1$-$C_6$ alkyl calcium alkoxide or $C_6$-$C_{12}$ aryl calcium alkoxide and when each occurrence of A or $R_1$ are substituted, the substituent is selected from —$(CH_2)_n OR'$ and —$(CH_2)_n NR'R'$, wherein n is an integer selected from 0 to 6 and R' is independently selected from H and $C_1$-$C_6$ linear alkyl chain, wherein the biodegradable calcium material is a controlled calcium-release material.

2. The biodegradable calcium material of claim 1, wherein 35%-55% of the total weight of said material is calcium.

3. The biodegradable calcium material of claim 1, wherein the calcium material is in the form of nanoparticles.

4. A method for the preparation of the biodegradable calcium material of general formula (I) of claim 1, comprising the steps of:

a) preparing at least one calcium alkoxyalkoxide of general formula $Ca(OAOR_1)_2$ in solid form, wherein A is a divalent $C_1$-$C_6$, optionally substituted, linear or branched alkyl chain and $R_1$ is a $C_1$-$C_6$ linear alkyl chain; and b) submitting the at least one calcium alkoxyalkoxide in solid form of step (a) to a temperature treatment of between 70° C. and 600° C.

5. The method according to claim 4, wherein in step (b) the calcium alkoxyalkoxide from step (a) is submitted to a temperature treatment of from 100° C. to 500° C.

6. The method according to claim 4, wherein in step (b) the calcium alkoxyalkoxide from step (a) is submitted to said temperature treatment for a time period of 1 to 24 hours, optionally from 6 to 14 hours.

7. The method according to claim 4, wherein the step (a) of preparing at least one calcium alkoxyalkoxide in solid form comprises the following steps:

a1. dissolving metal calcium at reflux temperature in an alkoxyalcohol of general formula $R_1OAOH$, wherein A is a divalent $C_1$-$C_6$, optionally substituted, linear or branched alkyl chain and $R_1$ is a $C_1$-$C_6$ linear or branched alkyl chain or $C_6$-$C_{12}$ aryl;

a2. optionally, cooling down to room temperature;

a3. diluting with an organic solvent;

a4. adding an aqueous base; and a5. ageing the solution obtained in step (a4) at room temperature.

8. The method according to claim 7, wherein the alkoxyalcohol of general formula $R_1OAOH$, is selected from the group consisting of those in which $R_1$ is methyl, ethyl, propyl or phenyl and A is a linear or branched, optionally substituted, $C_1$-$C_3$ alkyl chain, optionally, wherein $R_1$ is methyl, ethyl or phenyl.

9. The method according to claim 7, wherein the organic solvent in step (a3) is selected from the group consisting of ethyl acetate, acetone, N,N'-dimethylformamide, dimethylsulfoxide, methanol, ethanol, 2-methoxyethanol, 2-ethoxyethanol, 2-methoxypropanol, 1-methoxy-2-propanol, 2-ethoxypropanol, 1-ethoxy-2-propanol, n-propoxypropanol, 1-Methoxy-2-methyl-2-propanol, 1-propoxy-2-propanol, 2-propoxy-1-propanol, 2-(2-ethoxyethoxy)ethanol, 2-isopropanol, n-butanol, hexane, heptane, octane, and combinations thereof.

10. The method according to claim 7, wherein the aqueous base in step (a4) is selected from the group consisting of ammonia, aniline, pyridine, triethylamine, sodium hydroxide, potassium hydroxide, or combinations thereof.

11. A biodegradable calcium material obtained by the method according to claim 4.

12. A biocompatible matrix comprising the biodegradable calcium material as defined in 1.

13. A method for regenerating tissues, optionally selected from the group consisting of wound healing, bone regeneration, skin regeneration, muscle regeneration, cardiac regeneration and promotion of vascularization by applying to said tissue the biodegradable calcium material as defined in claim 1.

14. A method for the cosmetic regeneration of hair by applying to said hair the biodegradable calcium material as defined in claim 1.

15. A method for regenerating tissues, optionally selected from the group consisting of wound healing, bone regeneration, skin regeneration, muscle regeneration, cardiac regeneration and promotion of vascularization by applying to said tissue the biocompatible matrix as defined in claim 12.

16. A method for the cosmetic regeneration of hair by applying to said hair the biocompatible matrix as defined in claim 12.

17. The method according to claim 7, wherein the organic solvent in step (a3) is ethanol.

* * * * *